(12) United States Patent
Zheng et al.

(10) Patent No.: US 11,754,652 B2
(45) Date of Patent: Sep. 12, 2023

(54) SYSTEMS AND METHODS FOR POLARIZED NUCLEAR IMAGING AND SPECTROSCOPY

(71) Applicants: Yuan Zheng, Fremont, CA (US); G. Wilson Miller, Charlottesville, VA (US); William A. Tobias, Charlottesville, VA (US); Gordon D. Cates, Gordonsville, VA (US); David Anthony Keder, Woodbridge, VA (US)

(72) Inventors: Yuan Zheng, Fremont, CA (US); G. Wilson Miller, Charlottesville, VA (US); William A. Tobias, Charlottesville, VA (US); Gordon D. Cates, Gordonsville, VA (US); David Anthony Keder, Woodbridge, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 847 days.

(21) Appl. No.: 16/333,811

(22) PCT Filed: Sep. 15, 2017

(86) PCT No.: PCT/US2017/051767
§ 371 (c)(1),
(2) Date: Mar. 15, 2019

(87) PCT Pub. No.: WO2018/053256
PCT Pub. Date: Mar. 22, 2018

(65) Prior Publication Data
US 2019/0257904 A1 Aug. 22, 2019

Related U.S. Application Data

(60) Provisional application No. 62/395,146, filed on Sep. 15, 2016.

(51) Int. Cl.
*G01R 33/56* (2006.01)
*A61K 49/08* (2006.01)
(Continued)

(52) U.S. Cl.
CPC .......... *G01R 33/5601* (2013.01); *A61K 49/08* (2013.01); *A61K 51/02* (2013.01);
(Continued)

(58) Field of Classification Search
CPC ....... G01T 1/29; G01T 1/1603; G01T 1/2985; G01R 33/46; G01R 33/481;
(Continued)

(56) References Cited

U.S. PATENT DOCUMENTS 3,546,575 A * 12/1970 Jeffries ................ G01N 24/006
324/304
4,047,037 A 9/1977 Schlosser et al.
(Continued)

FOREIGN PATENT DOCUMENTS

EP 1132756 A2 9/2001
EP 1132757 A2 9/2001

OTHER PUBLICATIONS

Myers ["Xenon-127m: A New Radionuclide for Applications in Nuclear Medicine", J Nucl. Med 1990; 31:489-492] (Year: 1990).*
(Continued)

*Primary Examiner* — Oommen Jacob
(74) *Attorney, Agent, or Firm* — Meunier Carlin & Curfman LLC

(57) ABSTRACT

Polarized nuclear imaging and spectroscopy systems and methods are disclosed. In some embodiments, nuclei of a radioactive substance are polarized such that the spins of the nuclei are oriented in a specific direction, to generate a polarized radioactive tracer with anisotropic gamma ray
(Continued)

emission. The radioactive substance is selected such that the degree of anisotropy is enhanced. A tracer is introduced into a living subject for delivery to a target area of interest in the subject. The tracer is delivered such that nuclear spin relaxation of the tracer is inhibited during transport of the tracer to the target area of interest. Gamma rays from the gamma ray emission are detected, and based on the detected gamma rays and properties associated with the anisotropic gamma ray emission, imaging data and/or spectroscopic data are obtained that are associated with the tracer in the subject. In some embodiments, a radioactive substance is delivered to a target area of interest in the subject and the nuclei of the radioactive substance are polarized following delivery of the radioactive substance to the target area of interest, such that the spins of the nuclei are oriented in a specific direction, to generate a polarized radioactive tracer with anisotropic gamma ray emission. Gamma rays are detected from the gamma ray emission, and based on the detected gamma rays and properties associated with the anisotropic gamma ray emission, imaging data and/or spectroscopic data are obtained that are associated with the tracer in the subject.

2 Claims, 14 Drawing Sheets

(51) Int. Cl.
  *G01R 33/26* (2006.01)
  *G01R 33/44* (2006.01)
  *G01T 1/16* (2006.01)
  *G01T 1/29* (2006.01)
  *A61K 51/12* (2006.01)
  *A61K 51/02* (2006.01)

(52) U.S. Cl.
  CPC .............. *A61K 51/12* (2013.01); *G01R 33/26* (2013.01); *G01R 33/445* (2013.01); *G01T 1/1603* (2013.01); *G01T 1/29* (2013.01)

(58) Field of Classification Search
  CPC .. G01R 33/5601; G01R 33/323; G01R 33/50; G01R 33/56; G01R 33/26; G01R 33/445; G01R 33/00–5601; G01N 24/081; G01N 2223/626–6265; A61K 51/12; A61K 51/02; A61K 49/08
  See application file for complete search history.

(56) References Cited

U.S. PATENT DOCUMENTS

| | | | |
|---|---|---|---|
| 4,345,207 A * | 8/1982 | Bertrand | G01R 33/46 324/308 |
| H12 H | 1/1986 | Bennett et al. | |
| 5,276,615 A | 1/1994 | Edmond et al. | |
| 5,545,396 A | 8/1996 | Albert et al. | |
| 5,608,221 A | 3/1997 | Bertelsen et al. | |
| 5,642,625 A | 7/1997 | Cates, Jr. et al. | |
| 5,779,637 A | 7/1998 | Palkovich et al. | |
| 5,785,953 A | 7/1998 | Albert et al. | |
| 5,789,921 A | 8/1998 | Albert et al. | |
| 5,809,801 A | 9/1998 | Cates, Jr. et al. | |
| 5,860,295 A | 1/1999 | Cates, Jr. et al. | |
| 5,929,446 A | 7/1999 | Plummer et al. | |
| 5,936,404 A | 8/1999 | Ladebeck et al. | |
| 6,008,644 A | 12/1999 | Eunbach et al. | |
| 6,031,373 A | 2/2000 | Szeles et al. | |
| 6,051,208 A | 4/2000 | Johnson et al. | |
| 6,123,919 A | 9/2000 | Albert et al. | |
| 6,241,966 B1 | 6/2001 | Albert et al. | |
| 6,346,229 B1 | 2/2002 | Driehuys et al. | |
| 6,358,194 B1 | 3/2002 | Van Deripe | |
| 6,818,202 B2 | 11/2004 | Pines et al. | |
| 6,942,467 B2 | 9/2005 | Deninger et al. | |
| 7,174,200 B2 | 2/2007 | Salerno et al. | |
| 7,402,813 B2 | 7/2008 | Ben-Haim et al. | |
| 7,718,971 B2 | 5/2010 | Tanaka | |
| 8,242,453 B2 | 8/2012 | Wieczorek | |
| 8,368,029 B2 | 2/2013 | Wagenaar et al. | |
| 8,723,128 B2 | 5/2014 | Takayama | |
| 2003/0036700 A1 | 2/2003 | Weinberg | |
| 2005/0089474 A1* | 4/2005 | Cremillieux | A61B 5/055 424/9.3 |
| 2005/0161606 A1 | 7/2005 | Balan et al. | |
| 2012/0002783 A1* | 1/2012 | Toyokawa | G01V 5/0008 378/57 |
| 2012/0232381 A1 | 9/2012 | Gilhuijs et al. | |
| 2013/0259805 A1 | 10/2013 | Bacskai | |
| 2013/0338490 A1 | 12/2013 | Wendler | |
| 2015/0174273 A1* | 6/2015 | Weber | A61K 51/0497 424/1.89 |
| 2016/0084971 A1* | 3/2016 | Cates, Jr. | G01R 33/46 250/303 |
| 2018/0271470 A1* | 9/2018 | Cai | A61B 6/4057 |
| 2019/0257904 A1* | 8/2019 | Zheng | A61K 51/12 |

OTHER PUBLICATIONS

Bonn ["Orientation of 199mHg by Optical Pumping Detected by y-Radiation Anisotropy", Z. Physik A 272, 375-380, 1975] (Year: 1975).*
Gaede ["High-Field Cross Polarization NMR from Laser-Polarized Xenon to Surface Nuclei", Appl. Magn. Reson. 8, 373-384 (1995)] (Year: 1995).*
Liu [Protection of center spin coherence by dynamic nuclear spin polarization in diamond, Nanoscale, 2014, 6, 10134], (Year: 2014).*
International Search Report and Written Opinion, issued in the related international application No. PCT/US2017/051767 dated Nov. 20, 2017.
Buchanan, M. et al., "A System to Obtain Radiotracer Uptake Data Simutaneously with NMR Spectra in a High Field Magnet," IEEE Transactions on Nuclear Science, IEEE Service Center, New York, NY, vol. 43, No. 3, Jun. 1996, pp. 2044-2048.
Zheng, Y. et al., "A Method for imaging and spectroscopy using [gamma]-rays and magnetic resonance," Nature, vol. 537, No. 7622, Sep. 28, 2016, London, pp. 652-655.
Extended European Search Report for European Application No. 15904290.2 dated Apr. 4, 2019, 10 pages.
Branca, R.T. et al., "Detection of human brown adipose tissue by MRI with hyperpolarized Xe-129 gas and validation by FDG-PET/MRI", Proceedings of the International Society for Magnetic Resonance in Medicine, 24th Annual Meeting & Exhibition, No. 1054, Apr. 22, 2016, Singapore.
Denis Duhamel et al., "Mesures de la perfusion cérébrale chez le rat à l'aide de la RMN du 129Xe hyperpolarisé: étude de fluides biologiques vecteurs du 129Xe", C.R. Acad. Sci. Chemie, Jan. 1, 2001, pp. 789-794.
Tseng, C.H et al., "Low-field MRI of laser polarized noble gas", vol. 81, No. 17, Oct. 26, 1998, pp. 3785-3788.
Marsden, P.K. et al., "A system to obtain radiotracer uptake data simultaneously with NMR spectra in a high field magnet", 1995 IEEE Nuclear Science Symposium and Medical Imaging Conference Record, 1995, vol. 3, pp. 1728-1731.
Supplemental European Search Report for European Application No. 17851596.1 dated Apr. 22, 2020, 10 pages.
Examination report No. 1 for standard patent application for Australian Application No. 2015409278 dated Jun. 12, 2020, 4 pages.
Examination Search Report for Canadian Application No. 2961361 dated Oct. 8, 2021, 6 pages.
Canadian Office Action issued in CA 2,961,361, dated Jul. 14, 2022.
Communication pursuant to Article 94(3) EPC issued in EP 17851596.1, dated Aug. 27, 2021.

(56) References Cited

OTHER PUBLICATIONS

Lerouge F. et al., "Towards thrombosis-targeted zeolite nanoparticles for laser-polarized 129Xe MRI", Journal of Materials Chemistry, 2009, vol. 19, pp. 379-386,.

Summons to attend to oral proceedings pursuant to Rule 115(1) EPC issued in EP 17851596.1, mailed Jan. 31, 2023.

Albert, M.S. et al., "Biological magnetic resonance imaging using laser-polarized 129Xe," Nature, 1994, pp. 199-201, 370(6486).

Calaprice, F. et al., "Nuclear Alignment and Magnetic Moments of 133Xe, 133Xem, and 131Xem by Spin Exchange with Optically Pumped 87Rb," Phys. Rev. Lett., 1985, pp. 174-177, 54(3).

Zheng, Y., et al., "A Method for Imaging and Spectroscopy Using Y-rays and Magnetic Resonance," Nature, vol. 537, Sep. 29, 2016, pp. 652-661; dol:10.1038/nature19775.

Driehuys, B. et al., "High-volume production of laser-polarized 129Xe," Appl. Phys. Lett., 1996, p. 1668, 69(12).

Kauczor, H. et al., "MRI using hyperpolarized noble gasses," Eur. Radiol. 1998, pp. 820-827, 8(5).

Myers, W.G. et al., "Krypton-79m: a new radionuclide for applications in nuclear medicine," J. Nucl. Med., 1986, pp. 1436-1441, 27(9).

Rabi, I.I., "Space Quantization in a Gyrating Magnetic Field," Phys. Rev., 1937, pp. 652-654, 51(8).

Walker, T.G. et al., "Spin-exchange optical pumping of noble-gas nuclei," Reviews of Modern Physics, 1997, pp. 629-642, 69(2).

Wu, Z. et al., "Coherent Nuclear-Spin Interactions of Adsorbed 131Xe Gas with Surfaces," Phys. Rev. Lett., 1987, pp. 1480-1483, 59(13).

Yamazaki, T., "Tables of coefficients for angular distribution of gamma rays from aligned nuclei," Nuclear Data Sheets, Section A, 1967, pp. 1-23, 3(1).

Zheng, Y. et al., "Very-low-field MRI of laser polarized xenon-129," J. Magn. Reson., 2014, pp. 108-117, vol. 249, Elsevier, Inc.

Berthault, P. et al., "Biosensing using laser-polarized xenon NMR/MRI," Prog. Nucl. Magn. Reson. Spectrosc., 2009, pp. 35-60, 55(1), Elesevier B.V.

Cappeller, U. et al., "Anisotropy and time modulation of y-radiation emitted by optically aligned 203Hg nuclei," J. Magn. Reson., 1969, pp. 15-21, 10(1), Elsevier Science B.V.

Ernst, R.R., "Nuclear Magnetic Resonance Fourier Transform Spectroscopy (Noble Lecture)," Angew. Chem. Int. Ed., 1992, pp. 805-823, 31(7), Nobel Foundation.

Jastram, P.S. et al., "Angular Correlation of Gamma Radiations from Oriented Nuclei," Phys. Rev., 1956, pp. 1381-1388, 101(4).

Lauterbur, P.C., "Image Formation by Induced Local Interactions: Examples Employing Nuclear Magnetic Resonance," Nature, 1973, pp. 190-191, vol. 242, Nature Publishing Group.

Mugler III, J.P et al., "Simultaneous magnetic resonance imaging of ventilation distribution and gas uptake in the human lung using hyperpolarized xenon-129," Proceedings of the National Academy of Sciences, 2010, pp. 21707-21712, 107(50), National Academy of Sciences.

Mugler III, J.P et al., "Hyperpolarized 129Xe MRI of the human lung," J. Magn. Reson. Imaging, 2013, pp. 313-331, 37(2), Wiley Periodicals, Inc.

Rabi, I.I. et al., "A New Method of Measuring Nuclear Magnetic Moment," Phys. Rev., 1938, p. 318, 53(4).

Rodriguez, J. et al., "Determination of spin, magnetic moment and isotopic shift of neutron rich205Hg by optical pumping," Z. Physik A., 1975, pp. 369-374, 272(4), Springer-Verlag.

Spence, M.M. et al., "Functionalized xenon as a biosensor," Proceedings of the National Academy of Sciences, 2001, pp. 10654-10657, 98(19), National Academy of Sciences.

Spiers, J.A., "Angular Distribution of Radioactive Disintegration Products," Nature, 1948, pp. 807-809, vol. 161, Nature Publishing Group.

Tolhoek, H.A. et al., "Angular distribution and polarization of gamma radiation emitted by aligned radioactive nuclei," Physica XVIII, Letter to the Editor, 1952, pp. 357-358, No. 5.

Tolhoek, H.A. et al., "Angular Distribution and Polarization of Gamma Radiation Emitted by Oriented Nuclei," Physica XIX, 1953, pp. 101-119.

International Search Report and Written Opinion for related International Application No. PCT/US15/53403 dated Dec. 29, 2015.

Bonn, J. et al., Orientation of 199mHg by Optical Pumping Detected by Y-Radiation Anisotropy, Z. Physik vol. 272, pp. 375-380, 1974.

Myers, W., et al., Xenon-127m: A New Radionuclide for Applications in Nuclear Medicine; The Journal of Nuclear Medicine, vol. 31, No. 4 pp. 489-492, Apr. 1990.

\* cited by examiner

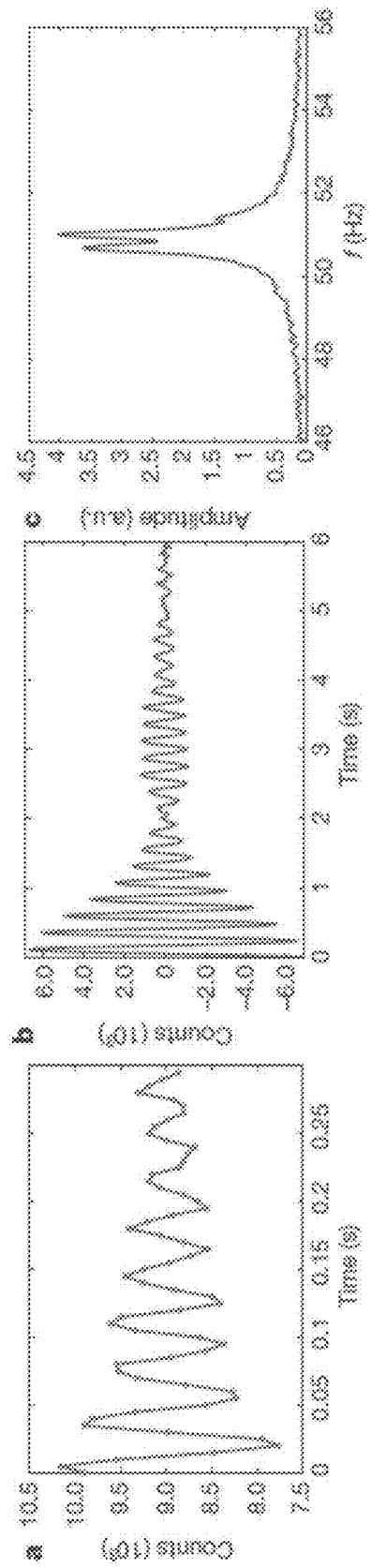

SYSTEMS AND METHODS FOR POLARIZED NUCLEAR IMAGING AND SPECTROSCOPY

CROSS-REFERENCE TO RELATED APPLICATION

This Application is a United States National Stage Application of, and claims the benefit pursuant to 35 U.S.C. § 371 of, International Patent Application Serial No. PCT/US2017/051767, which claims priority to and benefit of U.S. Provisional Patent Application Ser. No. 62/395,146 filed Sep. 15, 2016, the contents of both of which are hereby incorporated by reference herein in their entireties as if fully set forth below.

BACKGROUND

A wide variety of diagnostic techniques exist in the practice of medicine, including imaging modalities such as X-ray tomography, magnetic resonance imaging (MRI), and various nuclear-medicine imaging techniques. Molecular imaging techniques can use a tracer that is introduced to the body of a subject and selectively absorbed by parts of the body in which specific physiological processes are occurring. MRI can provide high detail, particularly of soft tissue. This technique may also be tailored so that contrast reflects morphology and also function and physiological processes. MRI can have the drawback, however, that a relatively large number of nuclear spins is needed to get reasonable signal-to-noise (SNR). Nuclear-medicine studies can utilize a variety of radioactive tracers that are explicitly introduced into the subject. These tracers can be chemically attached to various molecules that are selectively absorbed by the body, making it possible to probe specific processes or potential pathologies within the body. Detection can be accomplished through gamma-ray detection, and imaging may rely on the use of gamma-ray cameras with limited resolution.

It is with respect to these and other considerations that the various embodiments described below are presented.

SUMMARY

Some aspects of the present disclosure relate to systems and methods for polarized nuclear imaging and spectroscopy.

In one aspect, the present disclosure relates to a method for examining a target area of interest of a living subject. In one embodiment, the method includes polarizing nuclei of a radioactive substance such that the spins of the nuclei are oriented in a specific direction, to generate a polarized radioactive tracer with anisotropic gamma ray emission. The radioactive substance is selected such that the degree of anisotropy is enhanced. The method also includes introducing the tracer into a living subject for delivery to a target area of interest in the subject. The tracer is delivered such that nuclear spin relaxation of the tracer is inhibited during transport of the tracer to the target area of interest. The method further includes detecting gamma rays from the gamma ray emission, and obtaining, based on the detected gamma rays and properties associated with the anisotropic gamma ray emission, imaging data and/or spectroscopic data associated with the tracer in the subject.

In another aspect, the present disclosure relates to a method for examining a target area of interest of a living subject, and in one embodiment the method includes delivering a radioactive substance to the target area of interest in the subject. The method also includes polarizing nuclei of the radioactive substance, following delivery of the radioactive substance to the target area of interest, such that the spins of the nuclei are oriented in a specific direction, to generate a polarized radioactive tracer with anisotropic gamma ray emission. The method further includes detecting gamma rays from the gamma ray emission, and obtaining, based on the detected gamma rays and properties associated with the anisotropic gamma ray emission, imaging and/or spectroscopic data associated with the tracer in the subject.

In another aspect, the present disclosure relates to a system for examining a target area of interest of a living subject. In one embodiment, the system includes a polarizing system configured to polarize a radioactive substance such that the spins of the nuclei are oriented in a specific direction, to generate a polarized radioactive tracer with anisotropic gamma ray emission. The radioactive substance is selected such that the degree of anisotropy is enhanced. The system also includes a delivery system configured to introduce the tracer into a living subject for delivery to a target area of interest in the subject. The tracer is delivered such that nuclear spin relaxation of the tracer is inhibited during transport of the tracer to the target area of interest. The system further includes at least one gamma detector configured to detect gamma rays from the gamma ray emission. The system also includes a data acquisition system configured to obtain, based on the detected gamma rays and properties associated with the anisotropic gamma ray emission, imaging data and/or spectroscopic data associated with the tracer in the subject.

In another aspect, the present disclosure relates to system for examining a target area of interest of a living subject, and in one embodiment the system includes a delivery system for delivering a radioactive substance to the target area of interest in the subject. The system also includes a polarizing system configured to polarize nuclei of the radioactive substance, following delivery of the radioactive substance to the target area of interest, such that the spins of the nuclei are oriented in a specific direction, to generate a polarized radioactive tracer with anisotropic gamma ray emission. The system further includes at least one gamma ray detector configured to detect gamma rays from the gamma ray emission, and a data acquisition system configured to obtain, based on the detected gamma rays and properties associated with the anisotropic gamma ray emission, imaging and/or spectroscopic data associated with the tracer in the subject.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 3b is a diagram showing the pulse sequence used to make the image shown in FIG. 1a.

FIG. 4a is a plot of the counts per time bin measured in the transverse detectors while the polarized $^{131m}$Xe precessed in the x-y plane, analogous to a "free induction decay" in NMR. The raw data shown have been mixed down to a lower frequency to make the oscillations obvious at this time scale.

FIG. 4b is a plot of the counts (per 20 ms time bin) versus time in the longitudinal detector during Rabi oscillations, where the data were processed in a manner similar to those in FIG. 4a, except the time-averaged count rate has been subtracted from the down-converted signal.

FIG. 4c is a plot of the Fourier transform of the (unmixed) data shown in FIG. 4b. To obtain adequate statistics, these data were accumulated over multiple polarization cycles.

FIG. 5a is a plot under the condition of maximum RF field homogeneity, FIG. 5b is a plot under the condition of a somewhat inhomogeneous RF field, and FIG. 5c is a plot under the condition of even greater RF field inhomogeneity. RF field inhomogeneity was increased by increasing the separation of the RF coil pair, which is normally in a Helmholtz configuration. The measurements in FIG. 5b and FIG. 5c were acquired after lowering the bottom coil by 1 and 2 inches, respectively, without moving the upper coil or the sample. The splitting that is clearly visible in FIG. 5a gets progressively less pronounced in FIG. 5b and FIG. 5c. This result is consistent with the phenomenon of motional narrowing.

FIGS. 6a-6b are exemplary k-space data from polarized nuclear imaging, wherein FIG. 6a is the real part of k-space data from the longitudinal detector and FIG. 6b is the imaginary part of k-space data from the longitudinal detector, and wherein FIGS. 6a-6b result from one complete set of imaging data. The data shown in FIGS. 6a-6b were used to produce the image shown in FIG. 7a.

FIGS. 7a-7c are exemplary images of the "middle" cell (shown in FIG. 1b) from individual detectors, wherein each of FIGS. 7a-7c represent two complete averages, and wherein FIG. 7a is an image from the longitudinal detector with the highest analyzing power, FIG. 7b is an image from the transverse detector pointing at the sample from the left, and FIG. 7c is an image from the transverse detector pointing at the sample from the right.

DETAILED DESCRIPTION

Figure 1B:
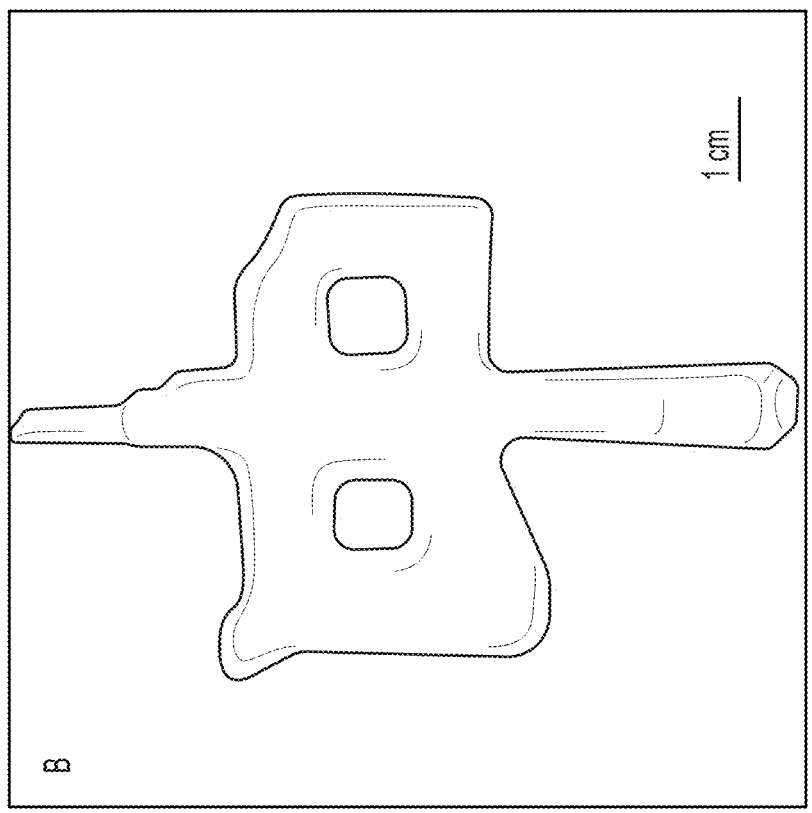
FIG. 1b shows a sealed glass cell, shaped like the Chinese character for "middle", in which a sample of $^{131m}$Xe is contained.

Some aspects of the present disclosure relate to systems and methods for polarized nuclear imaging and spectroscopy. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value. As used herein, "about" means within 20 percent or closer of a given value or range.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include patents, patent applications, and various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference.

As discussed herein, a "subject" or "patient" may be any applicable human, animal, or other organism, living or dead, or other biological or molecular structure or chemical environment, and may relate to particular areas of the subject (e.g., biological site), which may be referred to herein as an "area of interest", "target area", or "target area of interest". It should be recognized that while subjects described in some implementations of various aspects of the present disclosure described herein are biological or chemical in nature, some aspects of the present disclosure may be implemented to examine a variety of non-living subjects.

One or more data acquisition or data collection steps as described herein in accordance with one or more embodiments may include acquiring, collecting, receiving, or otherwise obtaining data such as imaging data and spectroscopy data corresponding to a subject. By way of example, data acquisition or collection may include acquiring data via a data acquisition device, receiving data from an on-site or off-site data acquisition device or from another data collection, storage, or processing device.

The following description provides a further discussion of certain aspects of the present disclosure in accordance with example embodiments. The discussion of some example implementations also refers to corresponding results which may include experimental data. Experimental data presented herein is intended for the purposes of illustration and should not be construed as limiting the scope of the present disclosure in any way or excluding any alternative or additional embodiments.

A discussion of some aspects and embodiments of the present disclosure that relate to polarized nuclear imaging and spectroscopy will now be described along with the corresponding FIGS. 1-11

Since Rabi first demonstrated nuclear magnetic resonance (NMR)[5], it has been understood that radio-frequency oscillating magnetic fields (RF) could be used to manipulate the orientation of nuclear spins. It is also well understood that the emission of gamma rays from oriented radioactive nuclei can be anisotropic[6-8]. Combining these phenomena, the application of RF on or near resonance has provided a useful tool for nuclear-physics studies involving anisotropic gamma emission, particularly for cases in which the nuclei were oriented using optical pumping techniques[9-12]. For example, such techniques have been used to precisely determine the magnetic moments of various radioactive nuclei including $^{131m}$Xe[12].

As will be discussed further with respect to aspects and embodiments of the present disclosure herein, anisotropic gamma emission has importance well beyond nuclear-physics studies and can provide the basis for powerful methods of signal detection for imaging and spectroscopy of radioactive nuclear tracers. Indeed, since even single gamma rays can be detected, the number of nuclei needed for meaningful measurements is vastly fewer than required for conventional NMR signal detection. Using, in part, techniques based from pulsed NMR[13], direct observations of nuclear spin precession are presented, as well as a form of spectroscopy. Further, an imaging modality referred to herein as polarized nuclear imaging (PNI) enables the visualization of tiny quantities of a nuclear tracer. Because PNI uses spatial-encoding techniques similar to MRI, the achievable image resolution is much finer than is currently practical in conventional nuclear imaging, which may use a collimated scintigraphic array (a "gamma camera") to determine the spatial origin of the detected gamma emissions[3].

Figure 1A:
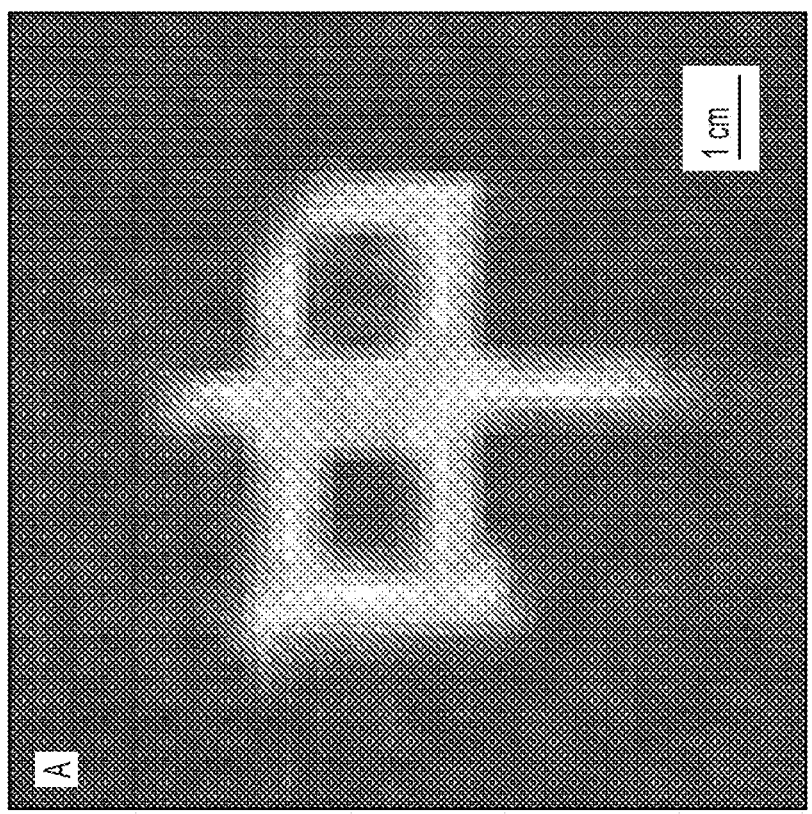
FIG. 1a is an image of roughly 1 mCi of $^{131m}$Xe obtained by combining magnetic-resonance techniques with the detection of gamma rays. The image is a 2D projection comprising 32×32 pixels, each 3 mm by 3 mm, and interpolated to 64×64 pixels for display.

FIG. 1a provides a high-resolution PNI image of ~4×10$^{13}$ laser-polarized $^{131m}$Xe atoms contained within the glass cell shown in FIG. 1b. The anisotropic emission of gamma rays from oriented nuclei can be characterized via the expression $$W(\theta_r) = \alpha_0 + \alpha_2 \cos(2\theta_r) + \alpha_4 \cos(4\theta_r) + \ldots, \quad (1)$$

where $W(\theta_r)$ is the relative probability that a given gamma ray will be emitted at an angle $\theta_r$ with respect to the direction of orientation. The values of the coefficients $\alpha_n$ depend on the particular isotope and gamma transition being observed, as well as the degree of nuclear polarization'. FIG. 2a is a plot of Eq. 1 for the 164 keV gamma transition of $^{131m}$Xe, for polarizations of 0%, 70% and 100% respectively. Although $^{131m}$Xe (spin 3/2) was used, there are many candidate tracers that may be utilized. However, only radioactive nuclei with spin >½ display the anisotropic gamma emission that is central to the detection scheme of some disclosed embodiments.

Figure 2B:
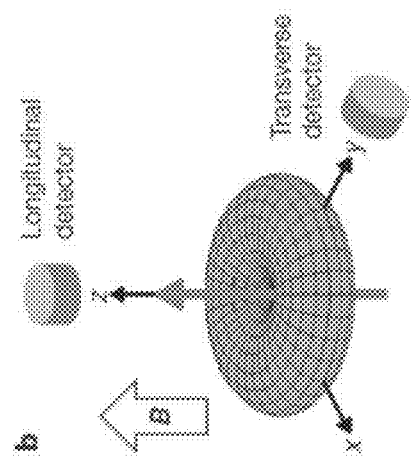
FIG. 2b is a 3D representation of eq. 1 for 100% polarized $^{131m}$Xe nuclei oriented along an applied magnetic field B. The count rate is minimum in the longitudinal detector and maximum in the transverse detector.
Figure 3B:
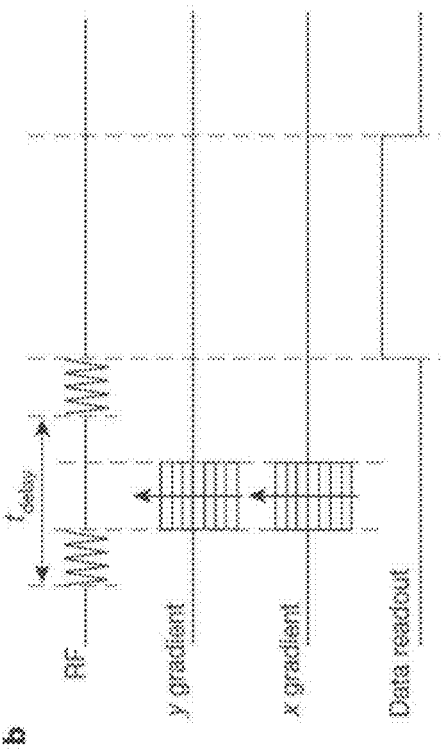
Figure 3A:
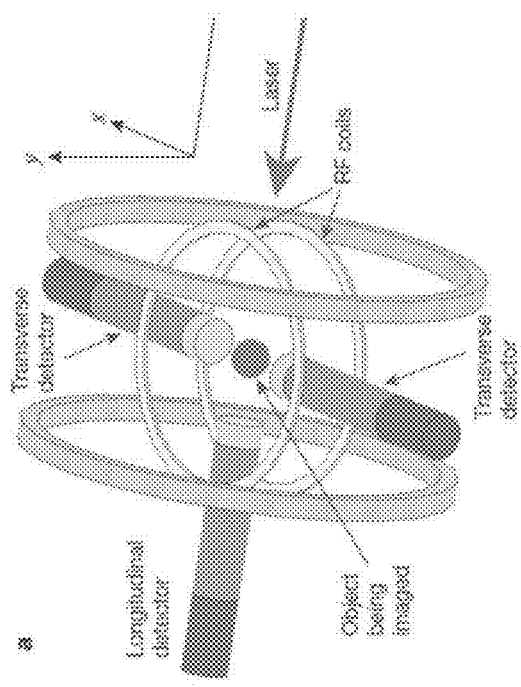
FIG. 3a illustrates the large (1.3-m diameter) Helmholtz coils that provided a static magnetic field along the z axis, the smaller (48-cm diameter) coils that provided an RF magnetic field along the y axis, and the transverse and longitudinal gamma detectors that were aligned with the x and z axes respectively. For imaging, two-dimensional spatial encoding along the x and y axes was accomplished using a gradient coil[15] (not shown). Circularly polarized laser light propagating along the z axis was used to polarize the $^{131m}$Xe samples.

Key elements of an imaging apparatus according to certain embodiments of the present disclosure are illustrated in FIG. 3a. In a particular implementation, large Helmholtz coils provided a holding field of 0.7 mT along the z axis, and smaller Helmholtz coils provided RF along the y axis. Three NaI detectors, one with a longitudinal orientation along the z axis and two with transverse orientations along the x axis, were used for gamma detection. Before imaging, spectroscopic measurements were performed in which gamma detection was used to directly observe polarized $^{131m}$Xe nuclear spin precession. Initially, with unpolarized spins, the count rates were nominally equal in all three detectors. The spins were then polarized along the z axis using the technique of spin-exchange optical pumping, and the buildup of polarization was monitored by observing a decrease (increase) in the count rate of the longitudinal (transverse) detector (FIG. 2b).

Figure 2C:
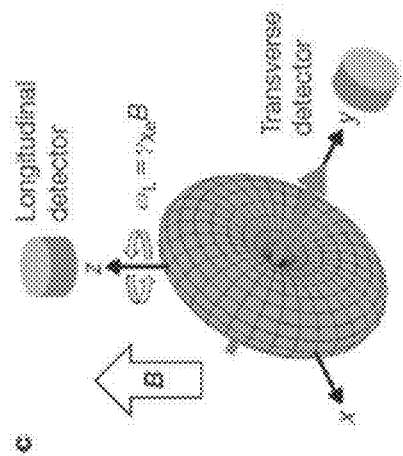
FIG. 2c graphically depicts the directional emission probability of 100% polarized $^{131m}$Xe nuclei oriented in the transverse (x-y) plane. The spin orientation, and thus the probability distribution, rotates about the z-axis at the Larmor frequency $\omega_L = \gamma B$. The count rate is maximum in the longitudinal detector and oscillates between minimum and maximum in the transverse detector with a frequency of $2\omega_L$.
Figure 2A:
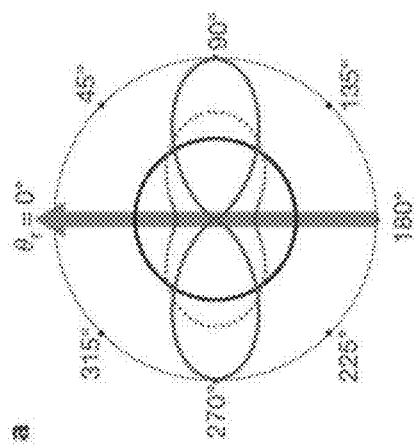
FIG. 2a is a polar plot of the directional emission probability (eq. 1) as a function of the angle $\theta_r$ with respect to the direction of orientation, for an ensemble of $^{131m}$Xe nuclei with polarization of 0%, 70%, and 100% respectively.

Once the polarization reached ~60%, which took 90-100 seconds (roughly three e-folding times), the spins were tipped into the transverse plane using a π/2 RF pulse (FIG. 2c). The spin orientation, and therefore the anisotropic emission distribution $W(\theta_r)$ then began to precess about the magnetic field, resulting in an oscillating count rate in the transverse detectors. This oscillation, which is analogous to a free-induction decay in NMR, is shown in FIG. 4a. The transverse coherence time was observed to be ~200 ms.

With conventional electromagnetic signal detection, NMR measurements can only be performed when the spins are actively precessing in the transverse plane. A transverse coherence time of 200 ms, however, limits the fractional spectroscopic resolution that can be achieved at the low magnetic field being used. The inventors used an alternative approach offering longer coherence times. When polarized spins are subjected to a transverse resonant RF field $B_1$, they precess about $B_1$ at a rate proportional to the RF field strength, causing the polarization along the longitudinal axis to oscillate. Typically, these so-called Rabi oscillations[16] are not directly observed. With gamma detection, however, it is quite natural to observe Rabi oscillations in the count rates of a longitudinal detector.

FIG. 4b shows the count rate in the longitudinal detector during Rabi oscillations. These longitudinal oscillations remained coherent for several seconds, which is an order of magnitude longer than the transverse coherence time seen in FIG. 4a. One or more "beat" frequencies are clearly visible, and the Fourier transform of the signal, shown in FIG. 4c, reveals at least two distinct frequency peaks. The observed data are reminiscent of those obtained by Wu et al.[17], who studied Rabi oscillations in a sample of nonradioactive $^{131}$Xe (spin 3/2). Wu et al. also observed multiple peaks, and demonstrated that they resulted from coherent quadrupole interactions with the glass walls of their anisotropic sample container.

Figure 5A:
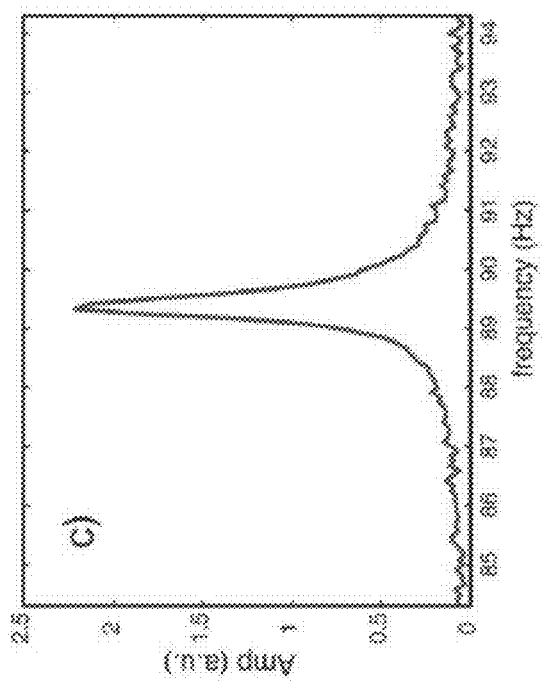
FIGS. 5a-5c illustrate the apparent motional narrowing in frequency spectra from Rabi oscillations, wherein the spectra are shown under three conditions.
Figure 5B:
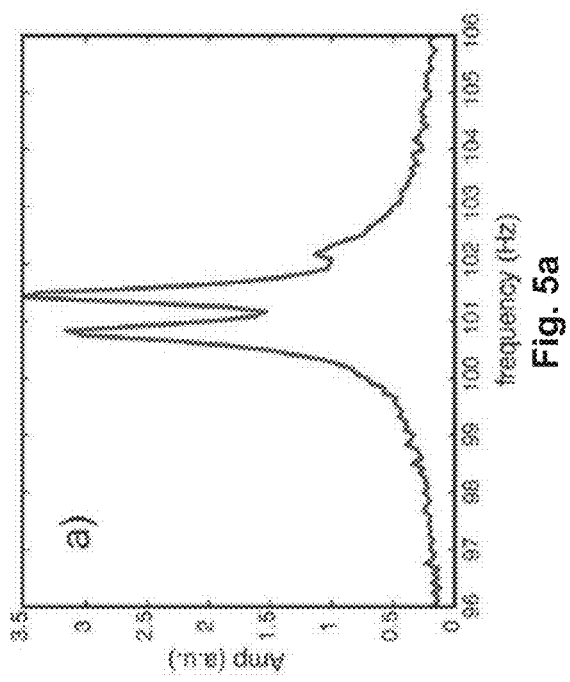
Figure 5C:
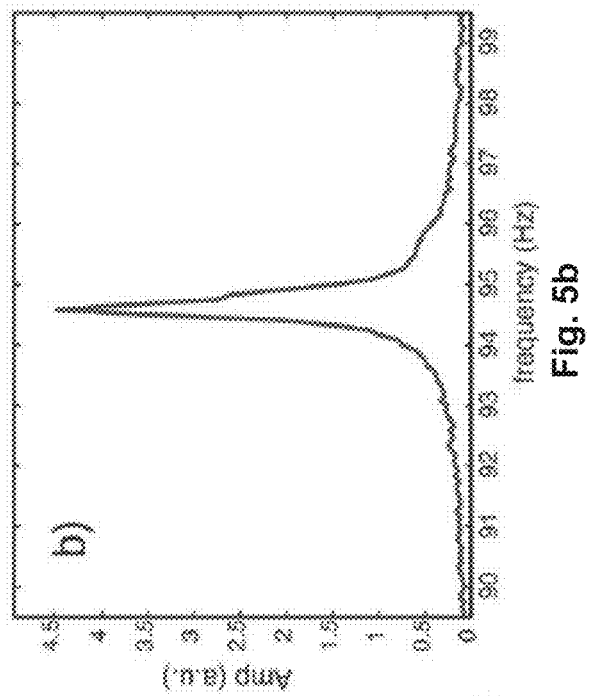

Because the inventors' "middle" cell was also highly anisotropic, and because the magnetic field inhomogeneities in the system were not large enough to explain the magnitude of the splitting, it was gathered that quadrupole interactions were causing the multiple peaks in the spectrum. The inventors were able to make the splitting disappear by intentionally increasing the RF field inhomogeneity (FIGS. 5a, 5b, and 5c). These data demonstrate the ability to resolve fine NMR spectral features using gamma detection.

Next, it will be discussed how the image shown in FIG. 1a was obtained. As is the case in MRI, data were acquired for points in "k space", where k represents a spatial frequency of the polarized spin distribution[2]. Before each data-acquisition cycle, the inventors polarized the $^{131m}$Xe sample to ~65%. The pulse sequence shown in FIG. 3b was then executed, which began with a π/2 RF pulse followed by the application (for a time τ) of a magnetic-field gradient described by $$\vec{G} = (\partial B_z/\partial x)\hat{x} + (\partial B_z/\partial y)\hat{y} \quad (2)$$

that provided sensitivity to a particular point in k space according to the relation $$2\pi \vec{k} = 2\gamma \vec{G} \tau. \quad (3)$$

Notable is the additional factor of 2 compared to the definition of k in MRI[2]. In principle, the resulting time-varying count rates in the transverse detectors contain the information required for image reconstruction, analogous to a fully phase-encoded image acquisition in MRI. With a transverse coherence time of 200 ms, however, the inventors were not able to accumulate enough statistics to resolve the amplitude and phase of these oscillations before the spins lost their coherence.

To overcome this limitation, the inventors developed an alternate approach which has no analog in MRI, for measuring the required spatial frequency components. A second π/2 pulse was applied after a time $t_{delay}$, which rotated the spins from the x-y plane into the y-z plane. As detailed more fully in the "Methods" section to follow, the resulting non-oscillating count rate in the longitudinal detector (whose coherence time is not limited by transverse spin dephasing) provided the required imaging information. For each point in k space, this cycle was executed twice using two values of $t_{delay}$ that differed from one another by ⅛ of the Larmor period. The resulting count rates, each of which were recorded for six seconds, are referred to as the real and imaginary spin moments, $S\Re(k)$ and $S_\Im(k)$ respectively. Extending the acquisition window beyond six seconds did not significantly improve image quality, most likely due to $T_2$ relaxation. Next, the following function is defined:

$$A(\vec{k}) = S\Re(\vec{k}) + iS_\Im(\vec{k}) - A_0 \quad (4)$$

where $A_0$ is a complex constant. For the appropriate choice of $A_0$, it can be shown that $$A(\vec{k}) \propto \int \rho(\vec{r}) e^{i\vec{k}\cdot\vec{r}} d^3\vec{r} \quad (5)$$

where ρ(r) is the density of polarized spins as a function of position r. By taking the Fourier transform of (5), the density distribution ρ(r) can be determined. This approach allows for the construction of an image using MRI-based spatial encoding without directly observing spin precession in the transverse plane, which is a unique characteristic of PNI with gamma detection.

The present disclosure, in accordance with certain embodiments, has potentially broad implications for research involving both biological and non-biological systems. In nuclear physics, polarization techniques have already been used for determining fundamental properties of radioactive nuclei[9-12], and the pulsed NMR techniques presented here can extend this research to include new observables and shorter-lived isotopes. Also, NMR is used to probe a wide variety of physical systems, and the present disclosure opens the possibility of using NMR techniques in situations where signal-to-noise ratio was previously a limitation. There are also implications for ongoing biomedical research that utilizes conventional magnetic resonance of hyperpolarized nuclei. Laser-polarized non-radioactive noble gases such as $^{129}$Xe have been used extensively for lung imaging[18,19]. Since xenon dissolves readily into blood, it is also possible to image polarized $^{129}$Xe in other well-perfused organs[20,21]. One approach to functionalize $^{129}$Xe as a biosensor involves trapping the $^{129}$Xe in a molecular cage tethered to a protein-specific ligand[21]. However, in vivo applications have been limited by the difficulty of polarizing and delivering sufficient quantities of material to distal parts of the body. Isotopes for which gamma detection is possible, however, offer the potential advantage of polarizing and delivering dramatically fewer particles.

There are several challenges involved in moving from in vitro to in vivo studies. Because of the relatively small amount of $^{131m}$Xe to work with in the above-described approaches (~1 mCi, much less than the typical activity used in a nuclear medicine procedure) and the relatively long half-life of this isotope (12 days), the inventors used multiple cycles of polarization and data acquisition to acquire the results. Clinical work may require faster acquisition protocols. A larger (but still medically acceptable) quantity of $^{131m}$Xe, together with a detector array with larger solid-angle coverage, may provide an increase in statistical power by a factor of ~500. As will be discussed more in the Methods section to follow, the shorter-lived isotopes $^{79m}$Kr and $^{127m}$Xe, both of which have been used previously for conventional nuclear imaging[22,23], may provide an increase in statistical power approaching 25,000.

In addition to considerations on obtaining adequate statistics in an acceptably short time appears possible, another consideration relates to the spin relaxation experienced in vivo by nuclei with spin >½. PNI in the gas phase may be feasible, as non-radioactive $^{83}$Kr (spin 9/2) has been successfully used for lung imaging[24]. In the dissolved phase, the challenge is identifying an agent with sufficiently slow relaxation. Whereas the longitudinal relaxation time ($T_1$) of $^{131m}$Xe in solution has not been studied, the $T_1$ of the stable isotope $^{131}$Xe (spin 3/2) in solution can be as short as a few milliseconds[25], which would be prohibitive. Fortunately, there are well over one hundred known nuclear isomers with sufficiently long half-lives[26] that may be polarized using dynamic nuclear polarization (DNP). Under favorable circumstances, nuclei with spin >½ can have $T_1$ values in solution of up to tens of seconds[27], and in the solid state, as high as hundreds of seconds[28]. Even if direct dissolved-phase imaging proves to be too difficult, encapsulating gas-phase particles in micro-bubbles[29] or the aforementioned molecular cages[21] may provide a basis for accessing biological targets outside the lung. As discussed more in the Methods section, there are a variety of specialized techniques that have been developed for hyperpolarized MRI that can be more effective in the current context. In addition to immediate non-biological applications of polarized nuclear imaging and spectroscopy, opportunities exist for a new class of medical diagnostics through the implementation of various aspects of the present disclosure.

Methods

Sample Preparation

Two different samples were prepared, each comprising a valved Pyrex glass cell containing a quantity of $^{131m}$Xe, a mixture of gases and several droplets of Rb. Each cell served as both the vessel in which the $^{131m}$Xe was polarized and the sample for the imaging or spectroscopy studies. The cell shown in FIG. 1b, which is shaped like the Chinese character for "middle" and measures roughly 5.5 by 6.5 cm, was used for the PNI and Rabi precession studies (FIGS. 1a, 4b, and 4c). A 2.5 cm diameter sphere was used for the FID measurement (FIG. 4a).

The $^{131m}$Xe used in the studies was the decay product of commercially available $^{131}$I. It was received in vials, roughly 10 cm$^3$ in volume, which in addition to $^{131m}$Xe contained a mixture of carrier gases (mostly nitrogen) at a pressure of roughly 1 atm. The gas contained in the vial was withdrawn into a syringe and then injected through a rubber septum into a small glass manifold attached to both an expandable bladder (consisting of a small Tedlar bag) and an evacuated valved Pyrex holding cell containing a few droplets of rubidium to act as a getter. The valve on the holding cell was initially closed. With the cell body dipped in liquid nitrogen, the valve was opened, drawing most of the gas from the bladder into the holding cell. The valve was then closed, and the holding cell was warmed to room temperature for several hours to allow the rubidium to combine with any reactive components of the carrier gas such as oxygen and water.

The purified gas was then transferred to a valved sample cell (which contained several droplets of fresh rubidium) by connecting the two cells and subsequently submerging the sample cell in liquid nitrogen. Prior to the transfer, a small quantity of (non radioactive) xenon, on the order of 1 Torr, was introduced to the sample cell to help facilitate the condensation of the trace amounts of $^{131m}$Xe. The valve on the sample cell was then closed, and the sample cell was connected to a larger evacuated cell. While the sample cell was kept in liquid nitrogen, the valve was briefly opened to bleed off as much of the carrier gas as possible. This last step may be repeated multiple times with freshly evacuated cells as often as needed. This approach for eliminating the carrier gas was chosen in order to minimize inadvertent releases of $^{131m}$Xe to the environment. The final step in preparing the sample cells was to add 150-400 Torr (see below) of $N_2$ and ~10 Torr of $H_2$. The $N_2$ was added to aid in the optical pumping process[4]. The small amount of $H_2$ was included to cause RbH to form on the cell's interior wall. RbH coatings have been shown to reduce nuclear spin relaxation in samples of (nonradioactive) $^{131}$Xe, most likely by reducing quadrupole interactions[30]. The "middle" cell initially contained roughly 1 mCi of $^{131m}$Xe and 150 Torr of $N_2$, and the spherical cell initially contained roughly 0.1 mCi of $^{131m}$Xe and 400 Torr of $N_2$. Additional details about the sample preparation can be found elsewhere[31].

Experimental Apparatus

The experimental apparatus made use of key components of an existing low-field MRI system that was previously used for conventional MRI of laser-polarized $^{129}$Xe (Zheng et al.[15]). Specifically, the laser system, oven, holding-field coil, RF transmit coil and gradient coils, along with their associated driving electronics, were largely identical to those described in Zheng et al.[15]. However, those portions of the previous apparatus related to signal detection were not used for the present study. It should also be emphasized that the number of $^{131m}$Xe atoms contained in the PNI phantom was smaller by a factor of roughly $4\times10^6$ compared with the number of $^{129}$Xe atoms imaged in Zheng et al.[15].

Imaging and spectroscopic data were acquired using the three gamma detectors shown in FIG. 3a. Each gamma detector consisted of three parts: a sodium-iodide (NaI) crystal, a light guide, and a photomultiplier tube (PMT). Each NaI crystal (2-inch diameter for the FID measurement; 3-inch diameter for the PNI and Rabi precession studies) was placed 13 cm from the center of the sample and was coupled to the PMT by an acrylic light guide approximately 1 meter long. Long light guides were used to keep the sensitive PMTs outside the 0.7 mT holding field and also to ensure that the magnetic shielding in the PMTs did not disturb the magnetic field at the sample.

The output signal from each PMT was first fed to a shaping amplifier (Spectroscopy Amplifier Model 2020, Canberra Industries, Meriden, Conn.) set to use a time constant of 0.25 µs. The output of the shaping amplifier was then sent to a discriminator (Timing Single-Channel Analyzer Model 420, Ortec, Oak Ridge, Tenn.) whose peak-height acceptance window was set so that 164 keV gamma rays from the $^{131m}$Xe were accepted, and background events (mostly consisting of ~30 keV x-rays) were largely rejected. For each accepted event, the discriminator generated a digital pulse which was sent to a gate/delay generator (Quad Gate/Delay Generator Model 794, Phillips Scientific, Mahwah, N.J.) to trigger a second digital pulse of adjustable width set to 3 µs. A data acquisition card (PCI-6259, National Instruments Corporation, Austin, Tex.) recorded the outputs of the gate/delay generators from all three detectors as a function of time, using three separate input channels. The data sampling frequency (333 kHz) was set to the inverse of the pulse duration, so that each gamma arrival resulted in a non-zero signal in exactly one time bin. Under the typical operating conditions, the gamma arrival rate was very low compared with the data sampling rate. As a result, the data stream was essentially binary, with only a small fraction of the time bins containing "1"s.

A magnetic holding field of 0.7 mT was used for the studies, corresponding to a Larmor frequency of 0.96 kHz. At the $^{131m}$Xe polarization levels with which the inventors worked (55-65%), only the terms $\alpha_0$ and $\alpha_2$ in Eq. 1 are non-negligible. Thus the count rates in the transverse detectors oscillated at 1.92 kHz (twice the Larmor frequency) during spin precession, which may be readily resolved at that data-sampling rate of 333 kHz.

The $^{131m}$Xe cell was housed inside a ceramic oven with glass windows located at the isocenter of the magnet system. Spin-exchange optical pumping was performed in-situ using 40 watts of laser power at an oven temperature of 140° C. (spherical cell) or 190° C. ("middle" cell). To estimate the $^{131m}$Xe polarization during spin-exchange optical pumping, the inventors monitored the count rate in the longitudinal detector, which decreased with increasing polarization (FIG. 2a). Under the typical running conditions, the time constant characterizing the build up of polarization was approximately 35 s. Since the resulting polarization levels were ~60%, this implies a $T_1$ in the absence of spin-exchange of ~90 seconds.

Acquisition Methods for Non-Imaging Studies

The inventors' non-imaging studies were performed using quantities of $^{131m}$Xe that were two to three orders of magnitude smaller than may be used for in vivo studies. Moreover, only 1-2% of the total solid angle was covered by each of the gamma detectors. For these reasons, the inventors used extensive signal averaging to obtain the results shown in FIG. 4. Because the half-life of $^{131m}$Xe is 12 days, however, acquiring additional averages only required repolarizing the contents of the cell, not refilling the cell with fresh $^{131m}$Xe.

For the FID results shown in FIG. 4a, the (unpolarized) 164 keV gamma count rate was ~900 Hz per detector and 1300 measurements were averaged. Prior to each measurement, the sample was polarized for 100 s, reaching a polarization level of ~55%. The laser was then blocked, a π/2 RF pulse was applied, and counts were recorded for 300 ms using the transverse detectors. Measurements were combined by adding the counts in corresponding time bins. The resulting time-varying signal was mixed down to a lower frequency for display, by multiplying with a sinusoidal function and applying a digital low-pass filter. Finally, the time-averaged count rate was added as an offset.

The Rabi precession experiment was performed using the same sample of $^{131m}$Xe that was used for the imaging experiment. By the time the Rabi precession experiments were performed, the original 1 mCi activity in the cell had declined to 0.3 mCi, yielding an unpolarized count rate of ~4.6 kHz in each detector. The results in FIGS. 4b and 4c show the average of 500 measurements. Prior to each measurement, the sample was polarized for 100 s, reaching a polarization level of ~65%. The laser was then blocked, the RF was turned on, and counts were recorded in the longitudinal detector for 6 s during the RF application. With a central oscillation frequency in the longitudinal detector of roughly 51 Hz, the amplitude of the applied RF was roughly 37.2 μT (or 18.6 μT for the RF in the rotating frame). Measurements were averaged in the same manner described above.

Formalism Behind the PNI Pulse Sequence

In this section, the theoretical formalism is described that shows how the pulse sequence illustrated in FIG. 3b provides for constructing an image by using gamma detection. It is assumed that the sample is initially polarized along the (longitudinal) z direction, and a π/2 pulse of RF is subsequently applied along the y direction, which rotates the spin orientation to point along the x direction. It is further assumed that while the spins are precessing in the (transverse) x-y plane, the sample is exposed to a linear magnetic-field gradient described by the vector:

$$\vec{G} = \frac{\partial B_z}{\partial x}\hat{x} + \frac{\partial B_z}{\partial y}\hat{y} \qquad (6)$$

After applying the gradients for a time τ, a spin located at position r will have precessed in the x-y plane by an angle φ given by $$\phi = \gamma(\tau \vec{G} \cdot \vec{r} + B_0 t), \qquad (7)$$

where t is the time elapsed following the π/2 pulse, $B_0$ is the strength of the holding field pointing along the z axis, and γ is the gyromagnetic ratio in units of radians per second per Tesla. For $^{131m}$Xe, $|\gamma/2\pi|$=1.37 MHz/T$^{12}$.

Next, the effect of a second π/2 pulse applied along the y axis at time t=$t_{delay}$ is considered. This RF pulse rotates the spins by 90° about the y axis, and whatever the azimuthal angle φ had been with respect to the x axis now becomes a polar angle $\theta_r$ with respect to the z axis. Let $\tau_L \equiv 2\pi/(\gamma B_0)$ be the Larmor period of the precessing spins. If $t_{delay}$ is a half-integral multiple of the Larmor period, $$t_{delay} = n\frac{\tau_L}{2} \qquad (8)$$

where n is a positive integer, the resulting polar angle with respect to the z axis will be given by $$\theta = \gamma\tau\vec{G}\cdot\vec{r} + n\pi. \qquad (9)$$

At this point in the pulse sequence, the polarized spins are precessing freely about the z axis. Although the azimuthal angle of the spin vector rotates at the Larmor frequency, its polar angle remains constant. And because the gamma emission probability only depends on the polar angle with respect to the spin orientation, the count rate in a longitudinally oriented detector is also constant (ignoring relaxation). Using Eq. 1 and retaining only the first two terms, the count rate in a detector oriented along the z axis, originating from a group of spins at position r, will be proportional to $$W = \alpha_0 + \alpha_2 \cos(2\gamma\tau\vec{G}\cdot\vec{r}). \qquad (10)$$

Next, the reciprocal k-space vector $$2\pi\vec{k} \equiv 2\gamma\tau\vec{G}. \qquad (11)$$

is defined. Notably, the extra factor of 2 here compared to the relationship between k and the gradient moment in conventional MRI$^2$, which is necessitated by the 2θ dependence in Eq. 1. $W_c(k,r)$ is defined to be the count rate originating from a group of spins at location r corresponding to a particular value of k. Thus, $$W_c(\vec{k},\vec{r}) = \alpha_0 + \alpha_2 \cos(2\pi\vec{k}\cdot\vec{r}), \qquad (12)$$

where the subscript c refers to the fact that with the choice of $t_{delay}$ given in Eq. 8, a cosine appears on the right-hand side of Eq. 12. Lastly, $W_c(k,r)$ is integrated over r to obtain a quantity referred to herein by the inventors as the sample's real spin moment corresponding to a particular value of k defined as $$S\Re(\vec{k}) = \int \rho(\vec{r})[\alpha_0 + \alpha_2 \cos(2\pi \vec{k} \cdot \vec{r})] d^3\vec{r}. \quad (13)$$

Next is considered a second value of the delay time $$t_{delay} = \frac{(n+1/4)\tau_L}{2} \quad (14)$$

that differs from the first by ⅛ of the Larmor period. For this value of $t_{delay}$, the resulting value of W is given by $$W_s(\vec{k}, \vec{r}) = \alpha_0 - \alpha_2 \sin(2\pi \vec{k} \cdot \vec{r}), \quad (15)$$

where the subscript s refers to the fact that with this choice of $t_{delay}$ one ends up with a sine on the right-hand side of Eq. 15. One can accordingly calculate what will be called the imaginary spin moment of the sample corresponding to a particular value of $\vec{k}$, defined as $$S_\Im(\vec{k}) = \int \rho(\vec{r})[\alpha_0 - \alpha_2 \sin(2\pi \vec{k} \cdot \vec{r})] d^3\vec{r}. \quad (16)$$

Both $S\Re(k)$ and $S_\Im(k)$ are real numbers and are proportional to the gamma-ray count rates in the longitudinal detector for the two choices of $t_{delay}$ (Eqs. 8 and 14) respectively. For the purposes of imaging, the values chosen for $t_{delay}$ are not unique; only the difference between the two values is important. To obtain maximum benefit from this approach, however, the delay times should be short compared with the transverse relaxation time.

Finally, one considers a complex function A(k), defined as $$A(\vec{k}) \equiv S\Re(\vec{k}) + iS_\Im(\vec{k}) - A_0 \quad (17)$$

where $S\Re(k)$ and $S_\Im(k)$ are the real and imaginary spin moments defined above and $$A_0 \equiv \alpha_0(1+i) \int \rho(\vec{r}) d^3\vec{r} \quad (18)$$

is a global offset that is independent of k-space location. Using Eqs. 13, 16, and 18 in Eq. 17:

$$A(\vec{k}) = \alpha_2 \int \rho(\vec{r}) e^{-i\vec{k}\cdot\vec{r}} d^3\vec{r}. \quad (19)$$

Thus A(k) and ρ(r) are a Fourier-transform pair up to a scale factor. This result is quite striking. The inventors have shown that by measuring a set of time-independent count rates in a single longitudinal gamma detector, it is possible to construct an image of the polarized spin distribution.

Next is the consideration of how to interpret data from an arbitrarily oriented detector. The count rate in a longitudinal detector is constant following the second RF pulse, because the angle between the spin vector and detector orientation remains constant as the spin precesses about the longitudinal axis. By contrast, the angle between the spin vector and a non-longitudinal detector changes as the spin precesses, resulting in an oscillating count rate in this detector until coherence is lost. The time-averaged count rate will be focused on here.

To understand how to extract k-space data from non-longitudinal gamma emissions, consider a detector oriented at a polar angle $\theta_d$ with respect to the z axis and azimuthal angle $\phi_d$ with respect to the x axis. $\theta_{\mathit{eff}}(t)$ is defined to be the angle between the direction of that detector and a precessing spin that is described by a polar angle θ and an azimuthal angle ϕ(t). It is straightforward to show that $$\cos\theta_{\mathit{eff}}(t) = \cos\theta_d \cos\theta - \sin\theta_d \sin\theta \cos[\phi(t) - \phi_d] \quad (20)$$

The count rate is again given by Eq. 1, where cos 2θ is replaced by $$\cos 2\theta_{\mathit{eff}}(t) = 2[\cos^2\theta_d \cos^2\theta + 2\cos\theta_d \cos\theta \sin\theta_d \sin\theta \cos(\phi(t) - \phi_d) + \sin^2\theta^d \sin^2\theta \cos^2(\phi(t) - \phi_d)] - 1. \quad (21)$$

After some algebra, the time average of $\cos 2\theta_{\mathit{eff}}$ is given by $$\langle \cos 2\theta_{\mathit{eff}} \rangle = \frac{1}{4}[-1 + \cos(2\theta_d) + (1 + 3\cos(2\theta_d))\cos(2\theta)]. \quad (22)$$

Following the same reasoning as that which led to Eq. 12, the time-averaged count rate in this case equals $$W_c(\vec{k}, \vec{r}) = \alpha_0 + \frac{1}{4}\alpha_2[\cos(2\theta_d) - 1] + \frac{1}{4}\alpha_2[3\cos(2\theta_d) + 1]\cos(2\pi\vec{k}\cdot\vec{r}). \quad (23)$$

Comparing with Eq. 12, one can see that the count rate still contains spatial frequency information, but the analyzing power is lower due to the smaller coefficient of the cos (2πk·r) term and the larger constant term ($a_2$ is negative for $^{131m}$Xe). In the limit of $\theta_d=0$, Eq. 23 reduces to Eq. 12. While there is clearly a benefit to using additional non-longitudinal gamma detectors to cover a larger solid angle, the reduced analyzing power indicated by Eq. 23 needs to be considered. For example, at $\theta_d=54.7°$ the analyzing power goes to zero.

It is worth noting the implications of Eq. 23 with regard to image quality under two scenarios that are referred to herein as the small-object and large-object limits. In the small-object limit, the object being imaged is small in comparison to the distance between the object and the detector. In this case, the size and position of a detector will influence its analyzing power, but will not limit the image resolution to the extent that terms in Eq. 1 with n>2 can be ignored. In the large-object limit, the object being imaged is large in comparison to the distance between the object and the detector. In this limit the angle $\theta_d$, and hence the analyzing power, of the detector is different for different points in the object, effectively resulting in a different "brightness" for different points of the object. While this certainly affects image quality, notably related effects exist in MRI in which the signal magnitude as seen by the receive coils varies across the field of view.

Acquisition Methods for Polarized Nuclear Imaging

The phantom shown in FIG. 1b was imaged using the approach described in the previous section. The image was acquired as a two-dimensional projection; no slice selection was used. The two π/2 RF pulses were identical, each having 5 ms duration. Pulses of magnetic-field gradients, each of 28 ms duration, were applied simultaneously along the x and y directions during the time between the first and second RF pulses. The gradient pulse amplitudes were stepped in uniform increments through two nested loops, to evenly sample a 32-by-32 symmetric k space matrix at 3 mm pixel resolution. The extreme gradient moments were ±60 ms·mT/m, corresponding to a square gradient amplitude of 2.1 mT/m. Count rates were measured for two different delay times ($t_{delay}$=35 ms and 35.13 ms, which were much less than the transverse coherence time of 200 ms) in order to measure the real and imaginary spin moments, respectively, at each k-space location. The total number of excitations needed for a complete image was 2048. Data were acquired using all three detectors. When the sample was not polarized, the 164 keV gamma count rate was ~13 kHz in each detector.

Prior to each k space acquisition, the $^{131m}$Xe sample was polarized for 90 seconds, reaching a polarization level of ~65%. The counts in each detector were then measured for 10 seconds, providing normalization data that were used during image reconstruction. Next the laser beam was blocked, and the pulse sequence of FIG. 3b was applied. Counts were accumulated for 6 s after the completion of the second RF pulse. The laser was then unblocked, and the cycle was repeated. The image shown in FIG. 1a is the average of the images acquired during two complete imaging cycles, one immediately after the other, using a single sample of 1 mCi of $^{131m}$Xe.

Notably, at the maximum gradient strength of 2.1 mT/m, the maximum strength of the concomitant magnetic field over our sample is on the order of 0.06 mT, which is a significant fraction of the holding field strength of 0.7 mT. It is known that such concomitant fields can affect image quality of conventional MRI, particularly at low holding field strengths, and it is likely that concomitant fields would affect PNI in similar ways. However, the effects of concomitant fields on the disclosed PNI scheme were not explored here, and no special measures were taken to account for or minimize such effects. If performing conventional MRI, the inventors estimate that the maximum spatial mis-registration caused by the concomitant fields present during the phase-encoding gradients would be less than half the pixel size of 3 mm Therefore, it is likely that any image distortion or blurring due to concomitant fields would not be obviously noticeable in the PNI image shown in FIG. 1a.

It is also worth noting that any limits on image quality due to gas diffusion arise not from the 6-second data-acquisition time, but from the time period (~30 milliseconds) the spins spend in the transverse plane during phase encoding. Assuming that the self-diffusivity of $^{131m}$Xe atoms in the "middle" cell is 0.9 cm$^2$/s, this implies that the mean one-dimensional diffusion distance during this time is 2 mm, which is also less than the PNI pixel size.

Image Reconstruction

Figure 6A:
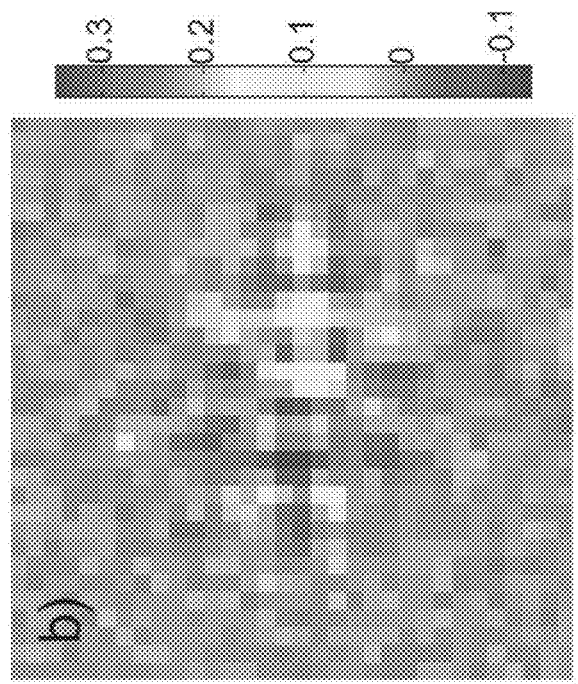
Figure 6B:
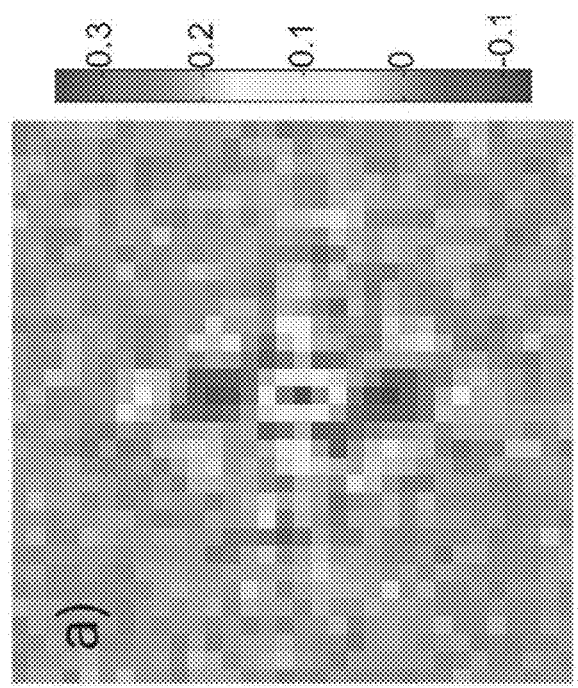
Figure 7C:
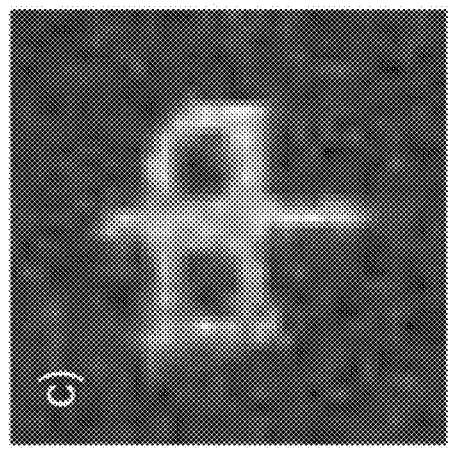
Figure 7B:
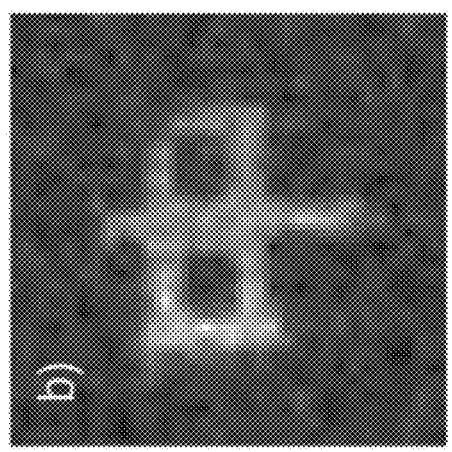
Figure 7A:
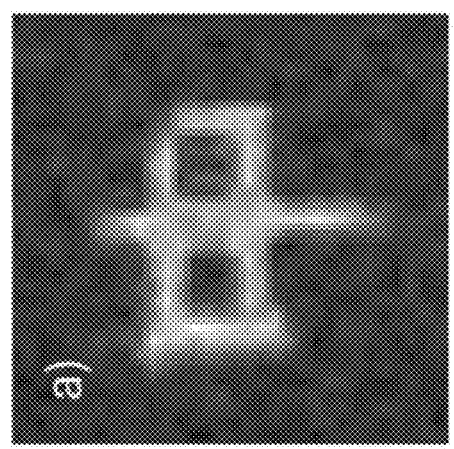

Data from each detector were analyzed independently. For each point in k space, there were two 6 s data strings, corresponding to the real and imaginary spin moments. To compensate for the decline of $^{131m}$Xe activity during the long imaging procedure, as well as any other slow drifts affecting the average count rate, the number of counts registered during each 6 s data string was divided by the baseline count rate measured before the first RF pulse. A 32-by-32 k-space matrix was constructed for each detector, and the normalized counts measured for each delay time were entered as the real and imaginary components at the corresponding k-space location. Before taking the Fourier transform, a complex-valued offset $A_0$ (see Eq. 17) was subtracted from every k-space entry. The appropriate value of $A_0$ was estimated from the average count rates measured around the periphery of k space. The k-space data for the longitudinal detector is shown in FIGS. 6a and 6b. Finally, a set of three complex images (one for each detector) were calculated by taking the inverse Fourier transform of each k-space matrix, and these images (shown individually in FIGS. 7a, 7b, and 7c) were combined using the standard sum-of-squares method[32] to arrive at the final magnitude image shown in FIG. 1a.

Considerations for In Vivo Applications

For non-biological applications, including nuclear physics studies where radiation dose is not an issue, there are numerous applications of the above-described embodiments, particularly with the ongoing construction of the U.S. Department of Energy Facility for Rare Isotope Beams[33]. For biological studies, especially in vivo studies, where radiation exposure is a significant factor of concern, there are a number of items to consider with respect to the above-described approaches.

One issue relates to statistics and acquisition time. In the image presented in FIG. 1a, the acquisition of one complete set of k-space data took ~60 hrs. Although most of this time was spent polarizing the $^{131m}$Xe, the total time during which k-space data were accumulated was ~200 min for a single image, which is considerably longer than a clinical MRI or nuclear imaging scan. Similarly, the spectroscopic studies described above required considerable averaging, which required acquiring data for more than a day. One consideration, accordingly, is isotopes that provide for such in significantly less time.

As mentioned earlier, the isotope $^{131m}$Xe was largely used in the studies described above because it was accessible. One way to reduce required acquisition time would be to increase the count rate by starting with a larger quantity of $^{131m}$Xe than the 1 mCi used. Furthermore, the solid-angle coverage provided by the detector array was ~6%. Even taking analyzing power into account, a factor of five improvement in counting statistics may be achieved by maximizing the solid-angle coverage. Thus, by using a 100 mCi sample of $^{131m}$Xe in combination with a full detector array, the data shown in FIG. 4b, which represents 500 averages, may be acquired in a single shot.

There are several characteristics to consider for isotopes to utilize in other implementations such as in vivo studies, rather than using $^{131m}$Xe. For in vivo studies, favorable isotopes would deliver higher statistics for a given radiation dose. The branching ratio of $^{131m}$Xe to the 161 keV gamma transition used in the above-described studies is about 2%, which means that 98% of the radioactive decays are not necessarily useful for imaging, although they do contribute to the total radiation dose. Furthermore, the biological half-life of xenon has been reported to be about five minutes, which is at least an order of magnitude longer than the expected lifetime of the nuclear polarization in vivo. Thus for $^{131m}$Xe, the radiation exposure to the subject would continue for much longer than the time during which useful statistics could be accumulated. In contrast, the isotopes $^{127m}$Xe (spin 9/2) and $^{79m}$Kr (spin 7/2) have gamma branching ratios of 38% and 27%, respectively[22,23], and radiological half-lives of around one minute, which are much shorter than their biological half-lives. These isotopes may thus provide around 50-100 times the counting statistics for a given radiation dose to the subject, compared with $^{131m}$Xe.

While further details on in vivo implementations will be provided below, in order to consider how image acquisition may proceed in vivo, it should be considered that it may be impractical to repolarize a sample of nuclei between acquisitions. While the point-by-point acquisition makes excellent use of the long half-life of $^{131m}$Xe, a more efficient strategy for sampling k space may be needed in vivo, for example by using echo techniques to obtain multiple lines of k space from each bolus of polarized nuclear tracer. One such acquisition strategy is described in the section "Alternative Imaging Approach" below. From the perspective of the number of counts alone, isotopes such as $^{127m}$Xe and $^{79m}$Kr can provide advantageous signal-to-noise (compared to FIG. 1a) with a medically acceptable dose of radiation.

The subject of spin relaxation in vivo will now be described. In the gas phase of the implementations and results discussed above, the $T_1$ measured for $^{131m}$Xe was often little different than the $T_1$ measured for $^{129}$Xe in a similar vessel. It appears that the quadrupolar spin relaxation of the $^{131m}$Xe was at least partly offset by the fact that its gyromagnetic ratio, and hence dipolar relaxation, is an order of magnitude smaller than for $^{129}$Xe. Duhamela et al.[29] measured the $T_1$ of $^{129}$Xe in micro-bubbles to be 20 seconds.

For enabling biomedical applications outside the lung, similar measurements may be made using $^{131m}$Xe. If $^{131m}$Xe is directly dissolved into an injectable liquid, however, the spin relaxation rate may be prohibitively fast because of its relatively large quadrupole moment[34]. This challenge may be shared by the other noble-gas isomers that have spin >½.

If laser-polarized noble-gases with nuclear spin >½ are unlikely to have long $T_1$ values in solution, the same limitation does not necessarily apply to other elements that may be polarized using DNP. Nuclei with relatively small quadrupole moments, particularly when part of a molecule with sufficient symmetry, can have $T_1$ values that are tens of seconds in the dissolved phase. Another approach is to embed the isomer in a suitable nanoparticle, as was recently demonstrated for hyperpolarized MRI of $^{29}$Si[35]. In that case the $^{29}$Si was found to have a $T_1$ of 600 seconds. While $^{29}$Si has a nuclear spin of ½, there are certainly examples of nuclei with spin >½ with long values of $T_1$ in the solid state. For example, $^{133}$Cs, which has a very small quadrupole moment, has been measured to have a $T_1$ of 330 seconds in CsH[28]. The flexibility to choose an isomer with a long $T_1$ when in the solid state, and incorporate that isomer into a biocompatible nanoparticle, can significantly expand the range of candidate nuclei.

There has been considerable interest in performing magnetic resonance studies of various nuclei that have been cross-polarized by other hyperpolarized nuclei, including both $^{129}$Xe and $^{13}$C[36,37,38]. The stable isotope $^{131}$Xe can be readily cross-polarized when closely surrounded by polarized $^{129}$Xe in solid form[39]. An approach that would keep $^{129}$Xe atoms in close proximity to atoms of an isomer such as $^{131m}$Xe or $^{127m}$Xe at body temperature can provide for delivering polarization in vivo using $^{129}$Xe, and inducing cross-polarization of the target nucleus immediately before data acquisition. A small quantity of an appropriate radioactive xenon isomer may be included within a larger sample of hyperpolarized $^{129}$Xe.

Further Discussion

A further discussion relating to PNI for in vivo settings, in accordance with some aspects of the present disclosure, will now be provided. As introduced in some detail above, there are challenges for medical diagnostic techniques in which a patient is exposed to radiation. When radiation plays a part in a medical diagnostic (as opposed to a medical treatment), it is necessary to limit the radiation to an acceptable level, that is, to a level that will not significantly increase the patient's probability to get cancer. At the very least, even if there is a slight increase, it is important to keep it to a minimum so that the benefits of the procedure outweigh the risk.

To address these challenges, in accordance with some embodiments of the present disclosure, the isotope selected for use in PNI is such that it has a large branching ratio to the gamma ray of interest. That is, when it radioactively decays, a large fraction of those decays should result in the gamma ray that will be detected when acquiring imaging data. For example, whereas the branching ratio for $^{131m}$Xe is only 2% to the gamma ray of interest, in contrast, the branching ratios to the gamma-ray of interest for $^{79m}$Kr and $^{127m}$Xe are 27% and 38% respectively. In choosing the isotope, it should be also selected such that the half-life is as short as practical, for example 10-20 seconds. Notably, certain nuclear medicine techniques use isotopes with half-lives that are in this range. For the cases of $^{79m}$Kr and $^{127m}$Xe, the half-lives are both right around one minute. While something even shorter may be contemplated and is within the scope of the present disclosure, in accordance with some embodiments, one minute is practical and allows for various practical aspects of the imaging to be more easily managed.

Further, as discussed in some detail above, it is known that nuclei with nuclear spin>½ in general have quadrupole moments, and that these quadrupole moments usually cause more rapid spin relaxation than is the case among nuclei for which the nuclear spin=½. This can be particularly pronounced when the atoms are in solution, or when the atoms are in a solid. In accordance with aspects of the present disclosure, there are several approaches that may be used to address this challenge. One such approach is to choose isotopes with very small quadrupole moments. Another approach is to choose isotopes that are imbedded in highly symmetric molecules. Also, isotopes may be chosen that have atomic properties which strike a good compromise between being sensitive to their chemical environment while not being so sensitive that they experience overly rapid spin relaxation. For example, $^{83}$Kr relaxes roughly 20 times more slowly when dissolved in n-Hexane than is the case for $^{131}$Xe.

Still another approach is to transport the isotope in vivo by encapsulating it in micro bubbles (or nanobubbles), a technique that has been demonstrated in normal MRI using hyperpolarized $^{129}$Xe (which is spin ½, but the principle is the same), or to transport the isotope in vivo by embedding it in a nanoparticle. Transportation via a nanoparticle has been demonstrated in normal MRI using hyperpolarized $^{29}$Si (which again is spin ½). The nanoparticle approach can be particularly attractive because, for example, very long spin relaxation times of $^{133}$Cs in a CsH salt have been shown[28]. Yet another approach is to not polarize the nuclei until they are already at the biological site of interest. The nuclei may be polarized using cross-polarization techniques in which appropriate RF pulses are applied to move polarization from a long-lived nuclear species to the radioactive isotope to be used for PNI. Cross polarization can work quite well when using nanoparticles.

A discussion of particular NMR properties of $^{83}$Kr and its use in PNI will now be provided. While the above-described studies were performed using $^{131m}$Xe, $^{79m}$Kr has attributes that make it an advantageous choice. Like both $^{131m}$Xe and the stable isotope $^{129}$Xe (which has been used extensively for noble-gas imaging), $^{79m}$Kr may be readily polarized by spin-exchange optical pumping (SEOP). It is well established that the stable isotope $^{83}$Kr can be polarized using SEOP, and the relevant parameters for doing so have been measured by Schaefer, Cates and Happer[40]. The isotope $^{83}$Kr has also been used in the past to image rodent lungs[24]. One observation by Schaefer, Cates and Happer[40] is that the T1 of $^{83}$Kr in the gaseous state was quite long in the samples that were studied, between 466 and 872 seconds in the small spherical glass cells that were used in the studies. These values of T1 are significantly longer than is typical for small glass cells containing $^{129}$Xe. Since the atomic (as opposed to nuclear) properties of krypton are quite central to determining T1, the T1 of $^{79m}$Kr may also be quite long. In the dissolved state, $^{83}$Kr has been measured to have a T1 of over 700 milliseconds in n-Hexane. Although a longer T1 would also be considered desirable, this is much longer than the T1 of $^{131}$Xe (also in n-Hexane) of tens of milliseconds, another noble gas isotope with a non-zero quadrupole moment.

As mentioned in some detail above, one approach to addressing the short T1 of noble-gas nuclei with non-zero quadrupole moments when in solution is in vivo imaging using microbubbles. For the case of $^{129}$Xe, the imaging of perfusion in rat brain was investigated by Duhamela et al.[29] using $^{129}$Xe that was both dissolved in a lipid suspension as well as contained in microbubbles. The T1 of the $^{129}$Xe in microbubbles was measured to be 20 seconds, more than long enough for in-vivo imaging, even when considering working with human subjects. The T1 of $^{83}$Kr has been found to be significantly longer than what can be observed under similar conditions when working with $^{129}$Xe. A microbubble may be an effective means of introducing $^{79m}$Kr into living subjects when interested in biological compartments beyond the lungs.

In accordance with one embodiment, an apparatus provides for imaging both gaseous noble-gas nuclei and also dissolved-phase noble-gas nuclei. The apparatus can be used to image dissolved phase $^{129}$Xe, and dissolved-phase images have been produced at dramatically lower magnetic fields than has ever been done previously. The apparatus has also been used to study $^{83}$Kr, and gas-phase images have been successfully made. The apparatus can also be used to produce dissolved phase images of $^{79m}$Kr where signal-to-noise can be boosted by huge factors, perhaps as much as one million. Another embodiment of the apparatus can be used to investigate the imaging of $^{79m}$Kr in microbubbles, for in vivo studies using $^{79m}$Kr outside of the lung.

Figure 8:
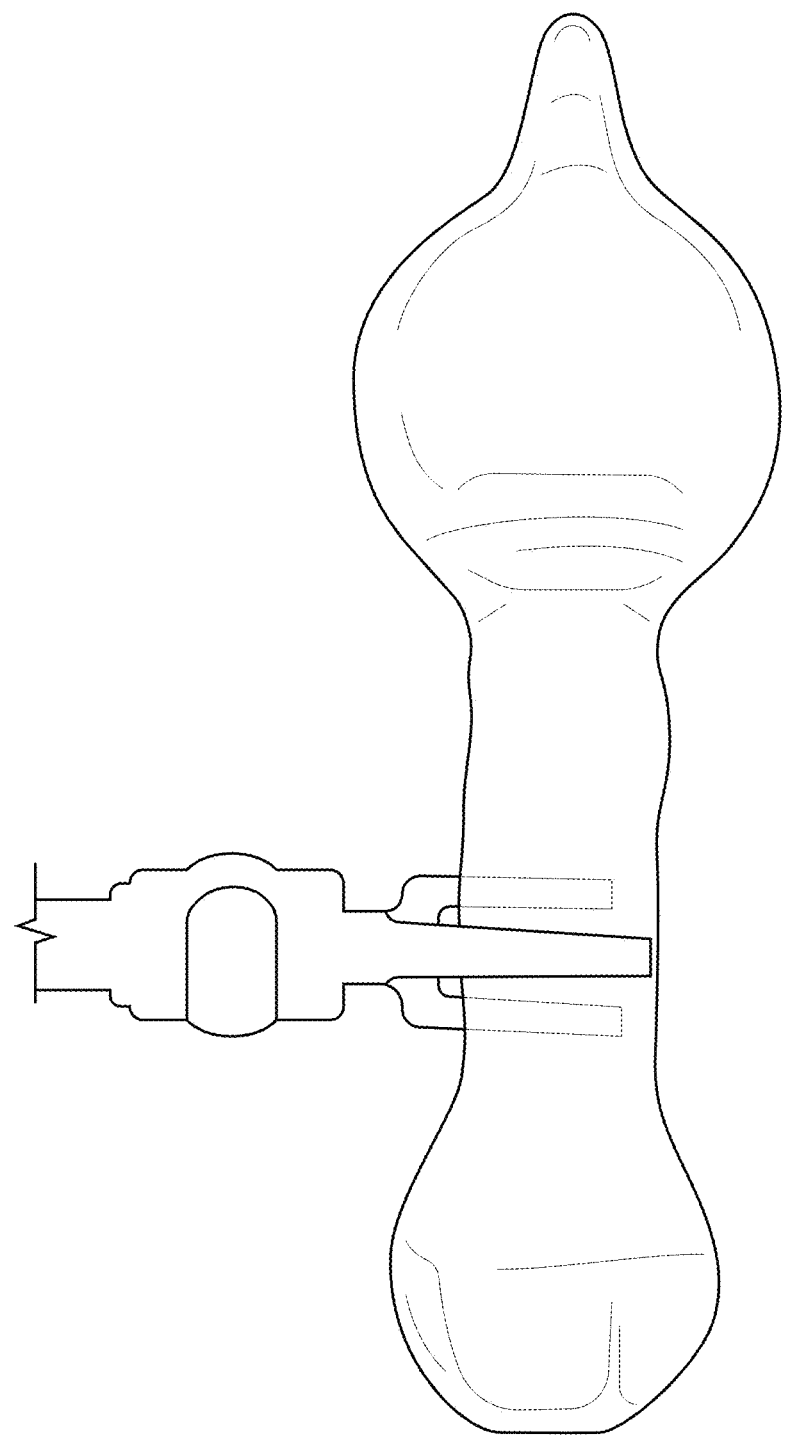
FIG. 8 shows an example of sealed glass cells used for studying gas-phase and dissolved phase images of $^{129}$Xe and $^{83}$Kr.

In accordance with some embodiments, an apparatus has sealed glass cells in which either $^{129}$Xe or $^{83}$Kr is polarized using SEOP while simultaneously allowing the gas to come into contact with sunflower oil. The cell may also be spun back and forth by a computer-controlled motor to agitate the oil and insure that the noble gas is mixed in with the oil more efficiently than would be the case from diffusion alone. An example of one of the cells is shown in FIG. 8. The cell was mounted in such a way that the upper portion can be illuminated by a laser (to polarize the noble gas), while the lower portion resided inside a small well-shielded solenoid coil that was used to perform pulsed NMR. Shielding was of importance because of the operation at low magnetic fields.

The cell was illuminated by roughly 80 Watts of light from spectrally-narrowed high-power diode-laser arrays in order to optically pump Rb vapor in the upper portion of the cell. After a period of one to several minutes, substantial nuclear polarization was achieved in the $^{129}$Xe or $^{83}$Kr, and pulsed NMR data were acquired. The cycle of polarizing the sample and acquiring pulsed NMR data may be repeated as many times as desired, making it able to acquire averaged spectra as well as images. Some aspects of the apparatus, such as configuration of the coils used to apply magnetic-field gradients, are described in Zheng, Y. et al.[15]

Figure 9:
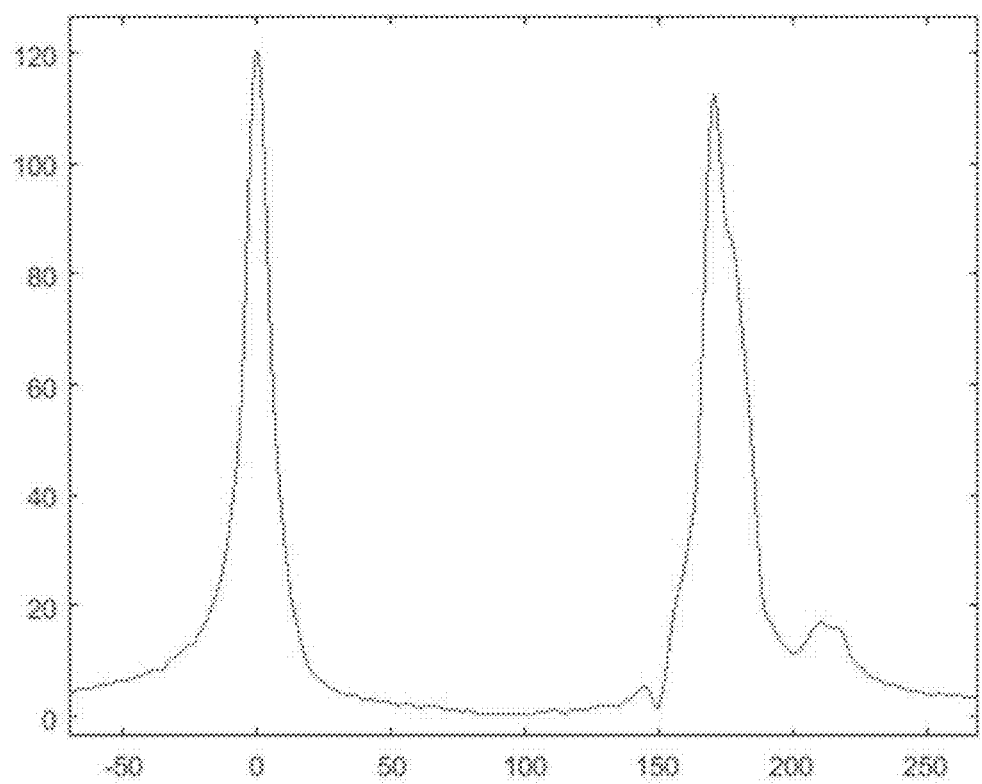
FIG. 9 depicts the frequency spectrum of $^{129}$Xe in the apparatus, which depicts well separated peaks for gas-phase and dissolved-phase signals.
Figure 10:
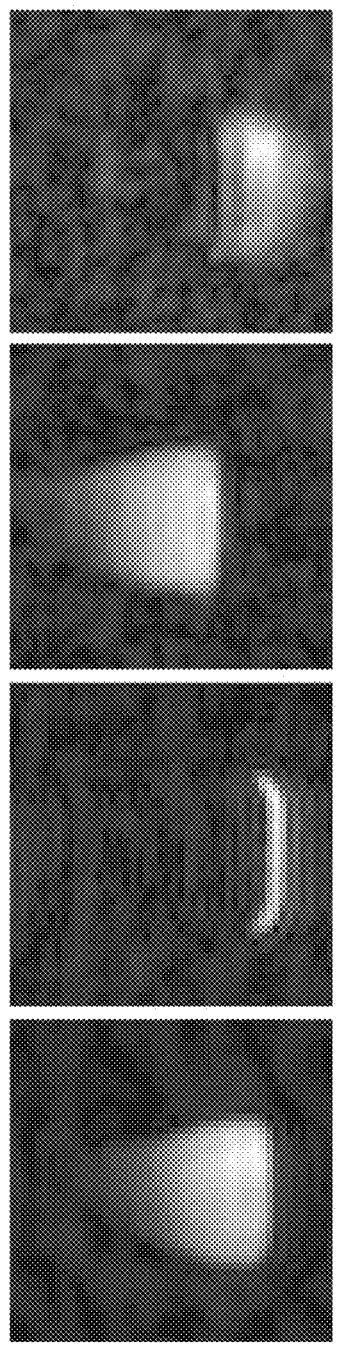
FIG. 10 shows four images of $^{129}$Xe obtained using a cell of the configuration shown in FIG. 8. The first two images (left) are of gas-phase and dissolved-phase $^{129}$Xe for the case in which no agitation was used. The second (right) images are of gas-phase and dissolved phase $^{129}$Xe for the case where agitation was used. In both cases, the interface between the gas and oil is clearly visible. It is also clear that, in the two dissolved-phase images, the $^{129}$Xe only penetrated the very top levels of the oil unless agitation was used.
Figure 11B:
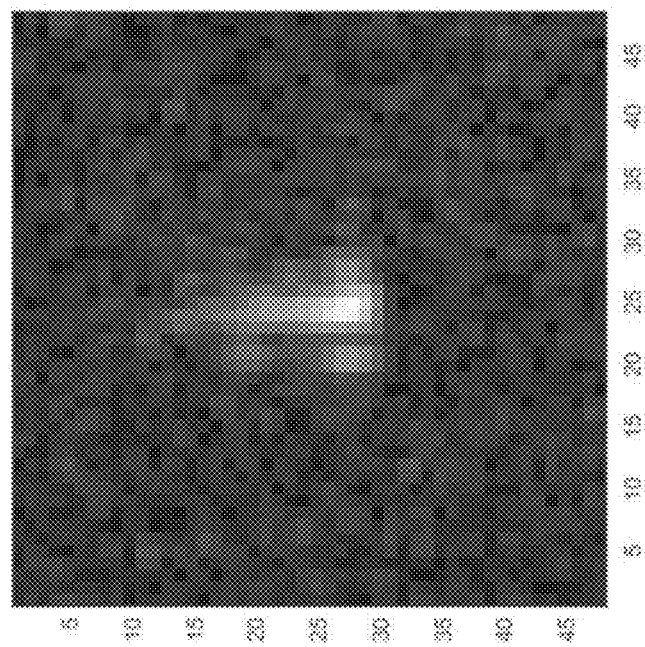
FIG. 11b shows a fully phase encoded image of the sample cell, shown without distinguishing between the gas-phase and dissolved-phase portions of the signal.
Figure 11A:
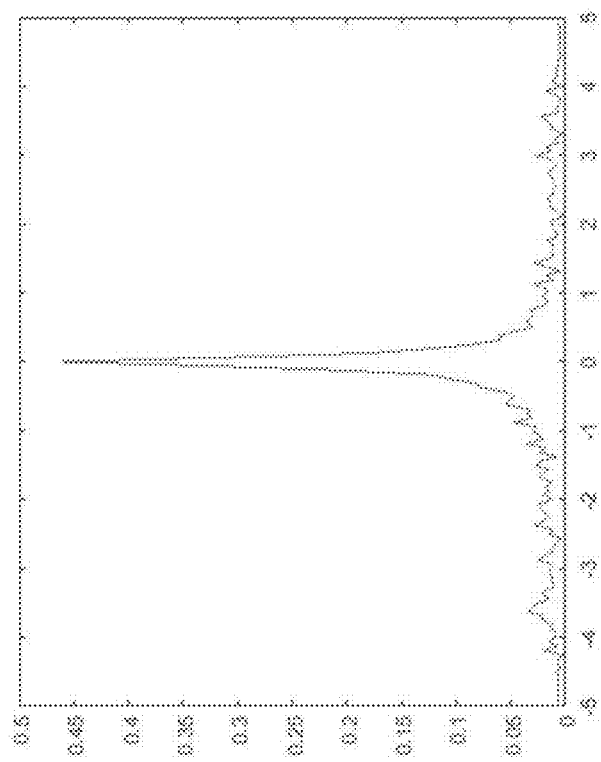
FIG. 11a shows a spectrum from $^{83}$Kr, where the gas-phase and dissolved-phase peaks are not able to be distinguished.

For the case of $^{129}$Xe, the NMR frequencies of the gas-phase and dissolved-phase signals were quite well separated, by roughly 200 ppm, as is indicated in FIG. 9. For imaging, a fully phase-encoded pulse sequence was used, making it possible to produce images of nuclei that were exclusively in either in the gas phase or the dissolved phase. Two dimensional images of the bottom portion of cells such as those shown in FIG. 8 were produced. An example of several images is shown in FIG. 10. Two pairs of images are shown, taken with and without agitation respectively. The first two images of FIG. 10 show the gas-phase and dissolved-phase images resulting when no agitation of the sample occurred. The interface between the gas and oil is clearly visible. It is also apparent that in the absence of agitation, the $^{129}$Xe penetrated only superficially into the oil. The second set of images in FIG. 10 corresponds to what resulted when agitation was used. It can clearly be seen that in this case the $^{129}$Xe was distributed much more extensively within the oil.

Alternative Imaging Approach

A discussion of further aspects and embodiments of the present disclosure that relate to polarized nuclear imaging will now be described along with corresponding FIGS. 12 and 13.

The above discussion with respect to certain implementations and results of certain embodiments of the present disclosure shown in FIGS. 1-11, describes the ability to image an intricate polarized spin distribution using only gamma detection, by using what amounts to a fully-phase-encoded acquisition scheme to sample individual points in k space and then applying the inverse discrete Fourier transform to reconstruct the image. This scheme, which was heavily informed by the inventors' knowledge of MRI, utilizes an initial 90° RF pulse to tip the spins into the transverse plane, followed by magnetic field gradients to generate sensitivity to a point in k space, and finally another 90° RF pulse to tip the spins back to longitudinal orientation for signal acquisition.

The inventors have developed an alternative strategy for image acquisition that is advantageously suited for in vivo use. A key feature of PNI is that imaging data (in the form of gamma count rates) can be acquired simultaneously with the application of RF, something that is generally not done in ordinary MRI. Moreover, in PNI it is not necessary to make use of MR spin precession in the transverse plane to encode spatial information. Instead, one can use spatially varying RF fields (which will be referred to herein as "$B_1$ gradients") to encode spatial-frequency information into the longitudinal orientation of the magnetization during Rabi oscillations. This approach takes advantage of the long coherence times observed during Rabi precession (on the order of seconds), as compared with the much shorter coherence times the inventors observed during free precession decay (on the order of hundreds of milliseconds).

The approach described in detail below allows an entire line of conjugate space to be read out one at a time. The term "conjugate space" is used herein to represent the spatial frequencies of the polarization distribution, rather than "k space", because the inventors believe it is more natural to base image reconstruction on the discrete cosine transform (DCT) rather than the Fourier transform, an approach that has been that has been suggested for MRI[41] but that has seen its widest applications in the area of image compression. Practical implementation of this alternative imaging strategy involves modifications to previous PNI apparatus described with respect to some embodiments discussed in earlier sections of this disclosure. The mathematical basis of the strategy is outlined next.

1D Imaging

The spatially anisotropic gamma emission probability W from a polarized nuclear tracer depends on the polar angle $\theta$ with respect to the direction of spin orientation: $W(\theta) \approx \alpha_0 + \alpha_2 \cos 2\theta$. Hence for a spatial distribution of spin isochromats $\rho(\vec{r})$, each of which is oriented at an angle $\theta(\vec{r})$ with respect to the longitudinal axis, the mean statistical count rate in a longitudinally oriented gamma detector is proportional to the integral of $W(\theta)$ over the sample:

$$R \propto \int [\alpha_0 + \alpha_2 \cos(2\theta(\vec{r}))] \rho(\vec{r}) d\vec{r}.$$

Next considered is the effect of a resonant $B_1$ field, with spatially varying amplitude, on the observed count rate. The magnitude of the $B_1$ field can be written:

$B_1 = B_1^0 + \vec{G}_1 \cdot \vec{r}$, where $B_1^0$ is a constant and $$\vec{G}_1 \equiv \frac{\partial B_1}{\partial x}\hat{x} + \frac{\partial B_1}{\partial y}\hat{y}$$

represents the $B_1$ gradient.

In the rotating frame, the spins precess about $B_1$ leading to a spatially dependent time-variation of the polar angle $\theta(\vec{r}, t) = \gamma B_1 t = \gamma t (B_1^0 + \vec{G}_1 \cdot \vec{r})$. That is, the Rabi precession frequency is a function of position in the transverse plane. The resulting time-dependent count rate in the longitudinal detector is given by $R(t) \propto \int [\alpha_0 + \alpha_2 \cos(2\gamma(B_1^0 + \vec{G}_1 \cdot \vec{r})t)] \rho(\vec{r}) d\vec{r}$.

The term $2\gamma B_1^0 t$ in the argument of the cosine can be viewed as the Rabi precession "carrier frequency," and needs to be eliminated in order to proceed with image reconstruction. For example, in a process somewhat akin to demodulation, $B_1^0$ can be set to an integer multiple of $\pi/\gamma\Delta t$, where $\Delta t$ is the readout time for each k-space sample. This causes the spins precess by an integral number of cycles during each time interval $\Delta t$, essentially locking the carrier frequency to the readout. Notably, every $\gamma$-ray count is recorded individually, so the subtleties of demodulation can also be examined retrospectively. Dropping the term with $B_1^0$, and defining the vector quantity $\vec{k}_1$ to be the time integral of the $B_1$-gradient amplitude according to:

$$\vec{k}_1 \equiv 4\frac{\gamma}{2\pi} \int \vec{G}_1(t) dt,$$

results in:

$R(\vec{k}_1) \propto \alpha_0 \int \rho(\vec{r}) d\vec{r} + \alpha_2 \int \cos(\pi \vec{k}_1 \cdot \vec{r}) \rho(\vec{r}) d\vec{r}$, which has the discrete analogy:

$R(k_1) = \alpha_0 \Sigma_{n=1}^N \rho(n) + \alpha_2 \Sigma_{n=1}^N \rho(n) \cos(\pi k_1 n)$ (24), where n represents the spatial position along the direction of the gradient. This expression is strikingly similar to the 1-dimensional inverse discrete cosine transform (DCT):

$$x(p) = \frac{1}{\sqrt{N}} X(1) + \sqrt{2/N} \sum_{n=2}^{N} X(n) \cos\left[\frac{\pi\left(p - \frac{1}{2}\right)(n-1)}{N}\right]$$

where $x(p)$ corresponds to $R(k_1)$ and $X(n)$ corresponds to $\rho(r)$. Thus by sampling the longitudinal count rate in the presence of a $B_1$-gradient of amplitude $G_1$ at the N time points $t=\frac{1}{2}\Delta t, \frac{3}{2}\Delta t, \ldots, (N-\frac{1}{2})\Delta t$, a 1D image can be reconstructed of the spin density distribution at the N spatial points $x=\Delta x, 2\Delta x, \ldots, N\Delta x$, by computing the DCT of the acquired $k_1$-space data. The relationship among $G_1$, $\Delta t$, $\Delta x$, and N satisfies $$4N\frac{\gamma}{2\pi} G_1 \cdot \Delta x \cdot \Delta t = 1.$$

Anisotropic vs. Isotropic Gamma-Ray Emission

Equation 24 shows that there will always be two components of the detector signal: a time-dependent part due to rotating polarized spins (corresponding to anisotropic emission) and a background due to unpolarized spins (corresponding to isotropic emission). This background count rate will increase as the polarization declines. The form of the cosine transform allows this background to be absorbed into the zero-frequency terms, which only affect the pixels at the upper and left edges of the image and are easily cropped out of the field of view. In effect, the DCT only "sees" the polarized component which is relevant to imaging.

Although this constant background does not necessarily interfere with the measurement of spatial frequencies in $k_1$-space, it does not contribute to their measurement either. In performing PNI, therefore, it is advantageous to keep the polarization decay rate as low as possible, both to enhance and maximize the useful (anisotropic) part of the detector signal and to minimize the unuseful (isotropic) part, which does not contribute to the PNI image acquisition but nonetheless contributes to the radiation dose to the subject. Furthermore, $^{131m}$Xe is probably not the ideal isotope for PNI, due to both its long half-life (12 days) and the fact that its branching ratio to the gamma-ray associated with anisotropic emission is only 2%. Thus 98% of the radioactive decays are not capable of anisotropic emission, and therefore contribute to the radiation dose but are not useful for PNI. An isotope with a larger branching ratio and shorter radiological half-life would be more favorable. One example is $^{127m}$Xe, which has a branching ratio of about 30% and a radiological half-life of about one minute[23], for which the useful count rates would be orders of magnitude higher for the same quantity of material.

2D Imaging

The two-dimensional inverse DCT is given by:

$$x(p, q) = \sum_{m=1}^{M} \sum_{n=1}^{N} A_m A_n X(m) X(n) \cos\left[\frac{\pi\left(p - \frac{1}{2}\right)(m-1)}{M}\right] \cos\left[\frac{\pi\left(q - \frac{1}{2}\right)(n-1)}{N}\right]$$

where $A_1 = 1/\sqrt{N}$, and $A_j = \sqrt{2/N}$ for $j > 1$. The one-dimensional acquisition scheme can be extended to allow two dimensional imaging by applying $B_1$ gradients along the perpendicular direction in the x-y plane, akin to phase encoding in MRI, before executing the readout $B_1$ gradient. The extension to two dimensions in PNI, however, has a complication. If $\theta_x$ is the phase accrued during the readout gradient $G_{1,x}$ and $\theta_y$ is the phase accrued during the perpendicular "phase-encode" gradient $G_{1,y}$, then the count rate will be proportional to $\cos \theta = \cos(\theta_x + \theta_y)$, whereas the cosine transform involves the product $\cos \theta_x \cos \theta_y$. (A similar issue does not exist in MRI, because $e^{i\varphi_1} e^{i\varphi_2} = e^{i(\varphi_1 + \varphi_2)}$.) But by invoking the trigonometric identity $2 \cos(\alpha) \cos(\beta) = \cos(\alpha+\beta) + \cos(\alpha-\beta)$, the inventors have found that the necessary product can be constructed by acquiring the same $k_{1,y}$ line twice, with opposite gradient amplitudes, and simply adding the data. The 2D image can then be reconstructed by applying the 2D DCT to the fully sampled $k_1$-space matrix.

Pulse Sequence Design

Figure 12:
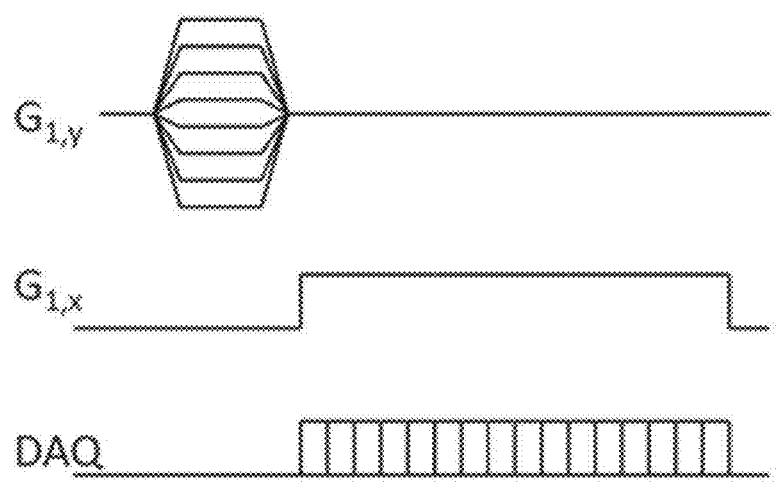
FIG. 12 is a diagram of a pulse sequence for acquiring PNI data using $B_1$ gradients and cosine-transform reconstruction.
Figure 13:
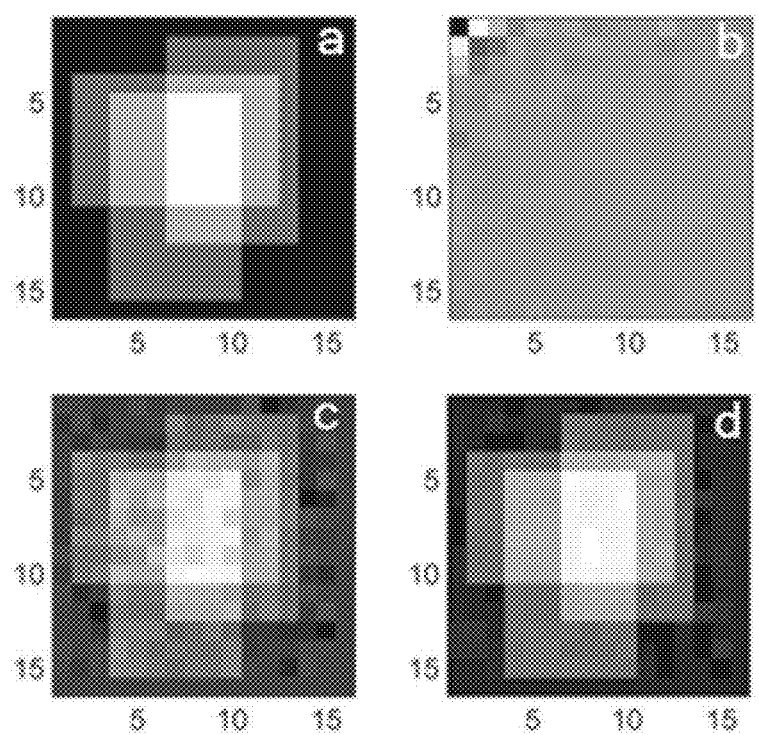
FIG. 13 show sample simulation results, wherein (a) shows an assumed spin density sampled on a 16-by-16 grid; (b) shows the $k_1$-space data matrix generated using our simulation of a 16-line acquisition with a total imaging time of 10 seconds, for a 10 mCi sample of $^{131m}$Xe; (c) shows the reconstructed image; and (d) shows the SNR improvement if a 100 mCi sample is assumed.

An appropriate pulse sequence for the 2D acquisition scheme is shown in FIG. 12. There are several notable differences from a two-dimensional pulse sequence for MRI: (1) Excitation and spatial encoding are part of the same process, so there is not a separate excitation RF pulse before the encoding gradients are applied. Moreover, data is acquired concurrently with RF application; (2) There is no pre-phaser lobe on the readout gradient $G_{1,x}$, because the cosine transform does not involve negative frequency components; (3) The data acquired using negative $G_{1,y}$ amplitudes are added to the data from the corresponding positive amplitudes; and (4) The amplitudes of the PE gradients follow the sequence (½, ³⁄₂, ⁵⁄₂, . . . ) rather than (0, 1, 2, . . . ).

Numerical Simulation

To validate the mathematical framework described above, MATLAB code was developed that simulates the time evolution of a given spin distribution under the pulse sequence described above, and computes the resulting $k_1$-space data for a given detector arrangement. The DCT2 function in MATLAB is then applied to reconstruct the simulated image of the spin distribution. By assuming the number of emissions seen by each detector in each time interval is governed by Poisson statistics, the image SNR can be predicted under different conditions (including voxel size, sampling time, polarization level, decay rate, and absolute particle density). In FIG. 13, (a) shows an assumed spin density sampled on a 16-by-16 grid; (b) shows the $k_1$-space data matrix generated using our simulation of a 16-line acquisition with a total imaging time of 10 seconds, for a 10 mCi sample of $^{131m}Xe$; (c) shows the reconstructed image; and (d) shows the SNR improvement if a 100 mCi sample is assumed.

Hardware Implementation

As described earlier, spatial gradients are introduced into the RF field rather than into the static magnetic holding field. The scheme is based on the ability to produce a circularly polarized RF field whose magnitude is a well-defined function of position in the transverse plane. This ensures that the Rabi precession frequency, in the presence of gradients, is a function of position. A straightforward way to accomplish this is to have two pairs of Helmholtz-like RF coils, aligned along the x- and y-axes respectively, which produce the spatially homogeneous RF field $B_1^0$, along with four gradient coils, which collectively produce the gradients of $B_1$ along the x and y directions. The x- and y-axis RF coils each need two gradient coils in order for the magnitude of $B_1$ to be time independent and a function solely of x and y.

The following briefly summarizes an arrangement that provides a spatial gradient in the magnitude of $B_1$. In short, each primary RF coil (x or y), that by itself produces a linearly polarized RF field, is equipped with two gradient coils so that the magnitude of the linearly polarized RF field can be a function of both x and y. One of these gradient coils can be nothing more than a few extra (counter-wound) turns on the primary coils producing the RF. The other gradient coil is oriented at the so-called "magic angle" $\theta_M=54.7°$ (the angle for which $\cos^2\theta=\frac{1}{3}$) with respect to the axis of the primary RF coil. The fact that coils with these orientations will provide the desired gradient tensors is discussed in detail by Cates et al.[42]. If the RF coils oriented along the x- and y-axes respectively are both equipped in this manner, and the magnitude of the gradients being produced by the different coils are all equal to one another, the desired control of the magnitude of $B_1$ is achieved. The x- and y-axis RF coils are run 90° out of phase with one another to produce circularly polarized RF.

Polarization System $^{131m}Xe$ is polarized in a manner suitable for dispensing from the polarization cell. For hyperpolarized gas MRI, considerable effort has gone into developing viable techniques for polarizing liter quantities of $^{129}Xe^{43,44}$. Because the amount of $^{131m}Xe$ needed for PNI is so small, however, a simple glass sphere, 2-3 cm in diameter, illuminated with a single 40 W spectrally narrowed diode laser array, is entirely sufficient to polarize the desired quantity to greater than 60%. The $^{131m}Xe$ polarization used to produce FIG. 1 was approximately 65%. A polarization system may include a simple oven to bring the cell to operating temperature, and a single NaI γ-detector to monitor polarization. The cell may have an input and output port, both of which may extend outside the oven. A dose may be dispensed by flushing the polarized $^{131m}Xe$ out of the polarization cell with a buffer gas such as $N_2$ or helium to yield a dose of $^{131m}Xe$ mixed with the buffer gas. Flushing is necessary because the polarization cell would likely operate below 1 atm.

Computing System

Figure 14:
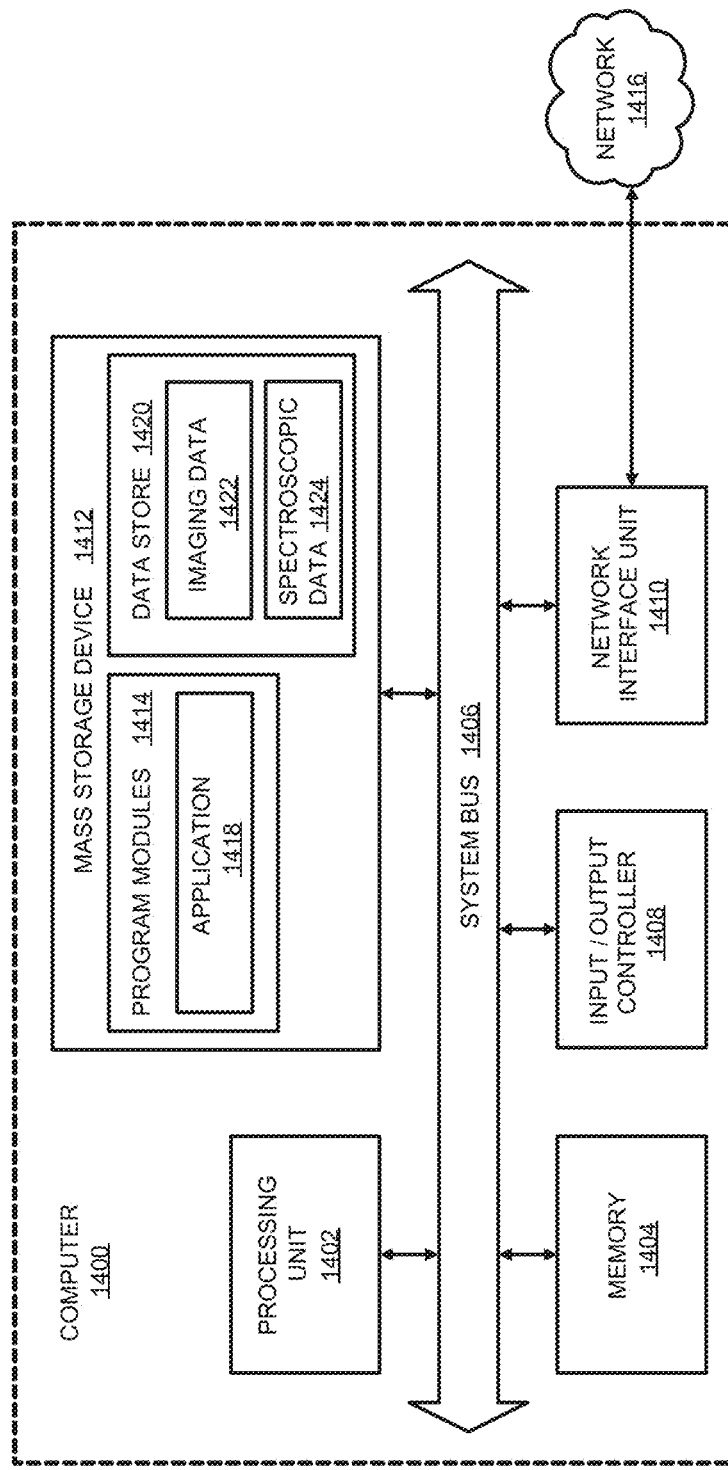
FIG. 14 is a computer architecture diagram showing a general computing system capable of implementing some aspects of the present disclosure in accordance with one or more embodiments.

FIG. 14 is a computer architecture diagram showing a general computing system capable of implementing aspects of the present disclosure in accordance with one or more embodiments described herein. A computer 1400 may be configured to perform one or more functions associated with embodiments illustrated in one or more of FIGS. 1-13. One or more components of the computer 1400 may be operatively coupled to the systems and apparatus shown in or associated with FIGS. 2, 3, and/or 8. It should be appreciated that the computer 1400 may be implemented within a single computing device or a computing system formed with multiple connected computing devices. The computer 1400 may be configured to perform various distributed computing tasks, in which processing and/or storage resources may be distributed among the multiple devices.

As shown, the computer 1400 includes a processing unit 1402 ("CPU"), a system memory 1404, and a system bus 1406 that couples the memory 1404 to the CPU 1402. The computer 1400 further includes a mass storage device 1412 for storing program modules 1414. The program modules 1414 may be operable to perform functions associated with embodiments illustrated in one or more of FIGS. 1-13 discussed above. The program modules 1414 may include an application 1418 for performing functions for obtaining and processing data, for example to obtain and process imaging and/or spectroscopic data associated with a subject, as described herein in accordance with various embodiments of the present disclosure. Further, the computer 1400 may be configured to control the various system and/or apparatus used for polarization of nuclei, application of RF magnetic fields and/or spatially varying magnetic fields, detection of gamma rays, and obtaining and/or processing imaging data and/or spectroscopic data in accordance with embodiments of the present disclosure described herein.

The computer 1400 can be configured to process data obtained by the gamma detector(s) in order to reconstruct an image of the spatial distribution of the tracer inside the subject and/or perform measurements of magnetic resonance properties of the tracer in the given environment, and the computer 1400 can be configured to, based on the obtained data, evaluate and diagnose various biological, chemical, or other processes or conditions of a subject, for example. The computer 1400 can include a data store 1420 for storing data that may include obtained imaging data 1422 and/or spectroscopic data 1424.

The mass storage device 1412 is connected to the CPU 1402 through a mass storage controller (not shown) connected to the bus 1406. The mass storage device 1412 and its associated computer-storage media provide non-volatile storage for the computer 1400. Although the description of computer-storage media contained herein refers to a mass storage device, such as a hard disk, it should be appreciated by those skilled in the art that computer-storage media can be any available computer storage media that can be accessed by the computer 1400.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 1400. "Computer storage media", "computer-readable storage medium" or "computer-readable storage media" as described herein do not include transitory signals.

According to various embodiments, the computer 1400 may operate in a networked environment using connections to other local or remote computers through a network 1416 via a network interface unit 1410 connected to the bus 1406. The network interface unit 1410 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems.

The computer 1400 may also include an input/output controller 1408 for receiving and processing input from any of a number of input devices and outputting data to output devices. Input devices may include one or more of keyboards, mice, stylus, touchscreens, microphones, audio capturing devices, and image/video capturing devices. An end user may utilize such input devices to interact with a user interface, for example a graphical user interface on one or more display devices such as display screens, for managing various functions performed by the computer 1400. The input/output controller 1408 may be configured to manage output to one or more output devices, including local or remote display devices such as display screens for presenting visual representations of data, and audio and/or video output devices.

The bus 1406 may enable the processing unit 1402 to read code and/or data to/from the mass storage device 1412 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state, or may include rotating media storing magnetically-encoded information. The program modules 1414, which include the application 1418, may include instructions that, when loaded into the processing unit 1402 and executed, cause the computer 1400 to provide functions associated with one or more embodiments illustrated in FIGS. 1-13. The program modules 1414 may also provide various tools or techniques by which the computer 1400 may participate within the overall systems or operating environments using the components, flows, and data structures discussed throughout this description.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is indicated by the appended claims, rather than the foregoing description, and all changes that come within the meaning and range of equivalents thereof are intended to be embraced therein.

REFERENCE LIST

[1] Lauterbur, P. C. Image Formation by Induced Local Interactions: Examples Employing Nuclear Magnetic Resonance. *Nature* 242, 190-191 (1973).

[2] Brown, R. W., Cheng, Y.-C. N., Haacke, E. M., Thompson, M. R., and Venkatesan, R. *Magnetic Resonance Imaging: Physical Principles and Sequence Design* (Wiley-Blackwell, Hoboken, 2014).

[3] Cherry, S. R., Sorenson, J. A., and Phelps, M. E. *Physics in Nuclear Medicine* (Elsevier Saunders, Philadelphia, 2012).

[4] Walker, T. G., and Happer, W. Spin-exchange optical pumping of noble-gas nuclei. *Rev. Mod. Phys.* 69, 629-642 (1997).

[5] Rabi, I. I., Zacharias, J. R., Millman, S. and Kusch, P. A New Method of Measuring Nuclear Magnetic Moment. *Phys. Rev.* 53, 318 (1938).

[6] Spiers, J. A. Angular Distribution of Radioactive Disintegration Products. *Nature* 161, 807-809 (1948).

[7] Tolhoek, H. A. and Cox, J. A. M. Angular distribution and polarization of gamma radiation emitted by oriented nuclei. *Physica* 19, 101-119 (1953).

[8] Jastram, P. S., Sapp, R. C. and Daunt, J. G. Angular Correlation of Gamma Radiations from Oriented Nuclei. *Phys. Rev.* 101, 1381-1388 (1956).

[9] Cappeller, U. and Mazurkewitz, W. Anisotropy and time modulation of γ-radiation emitted by optically aligned $^{203}$Hg nuclei. *J. Magn. Reson.* 10, 15-21 (1973).

[10] Rodriguez, J., Bonn, J., Huber, G., Kluge, H.-J. and Otten, E. H. Determination of Spin, Magnetic Moment and Isotopic Shift of Neutron Rich $^{205}$Hg by Optical Pumping. *Z. Physik A* 272, 369-374 (1975).

[11] Bonn, J., Huber, G., Luge, H.-J., Otten, E. W. and Lode, D. Orientation of $^{199m}$Hg by Optical Pumping Detected by γ-Radiation Anisotropy. *Z. Physik. A* 272, 375-380 (1975).

[12] Calaprice, F. P. et al. Nuclear Alignments and Magnetic Moments of $^{133}$Xe, $^{133m}$Xe, $^{131m}$Xe by Spin Exchange with Optically Pumped $^{87}$Rb. *Phys. Rev. Lett.* 54, 174-177 (1985).

[13] Ernst, R. R. Nuclear Magnetic Resonance Fourier Transform Spectroscopy (Nobel Lecture). *Angew. Chem. Int. Ed. Engl* 31, 805-930 (1992).

[14] Yamazaki, T. Tables of coefficients for angular distribution of gamma rays from aligned nuclei. *Nucl. Data Sect.* A 3, 1-23 (1967).

[15] Zheng, Y., Cates, G. D., Tobias, W. A., Mugler, J. P. and Miller, G. W. Very-Low-Field MRI of Laser Polarized Xenon-129, *J. Magn. Reson* 249, 108-117 (2014).

[16] Rabi, I. I. Space Quantization in a Gyrating Magnetic Field. *Phys. Rev.* 51, 652-654 (1937).

[17] Wu, Z., Happer, W. and Daniels J. M. Coherent Nucler-Spin Interactions of Adsorbed $^{131}$Xe gas with surfaces. Phys. Rev. Lett. 59. 1480-1483 (1987).

[18] Albert, M. S. et al. Biological Magnetic Resonance Imaging Using Laser-Polarized $^{129}$Xe. *Nature* 370, 199-201 (1994).

[19] Mugler, J. P. and Altes, T. A. Hyperpolarized $^{129}$Xe MRI of the human lung. *J. Magn. Reson. Imaging* 37, 313-331 (2013).

[20] Swansson, S. D., Rosen, M. S., Coulter, K. P., Welsh R. C., and Chupp T. E. Distribution and dynamics of laser-polarized $^{129}$Xe magnetization in vivo. *Magn. Reson. Med.* 42, 1137-1145 (1999).

[21] Spence, M. M. et al. Functionalized xenon as a biosensor. *Proc Natl Acad Sci U.S.A.* 98, 10654-10657 (2001).

[22] Myers W. G., Dahl, J. R., and Graham, M. C. Krypton-79m: A New Radionuclide For applications in Nuclear Medicine. *J. Nucl. Med.* 27, 1436-1441 (1986).

[23] Myers, W. G., Dahl, J. R., and Graham, M. C. Xenon-127m: A New Radionuclide for Applications in Nuclear Medicine. *J. Nucl. Med.* 31, 489-492 (1990).

[24] Galina E. Paviovskaya et al., Hyperpolarized krypton-83 as a contrast agent for magnetic resonance imaging, Proc. Natl. Acad. Sci. U.S.A. 102, 18275-18279 (2005).

[25] Luhmer, M. and Reisse, J., Quadrupole NMR relaxation of the noble gases dissolved in simple liquids and solutions: A critical review of experimental data in light of computer simulation results, Progress In Nucl. Mag. Res. Spectroscopy 33, 57-76 (1998).

[26] Jain, A. K. et al. Atlas of Nuclear Isomers, Nuclear Data Sheets 128, 1-130 (2015).

[27] Manfred Holz, New Developments in NMR of Simple Electrolyte Solutions, Progress in NMR Spectroscopy 18, 327-403 (1986).

[28] Saam, B., Pulse-NMR Studies of Spin Relaxation Relevant to Laser-Polarized Noble Gases, Ph.D. thesis, Princeton University (1995).

[29] Duhamela, G., Choquetb, P., Grillona, E., Leviela, J.-L., Zieglera, A. and Constantinescob, A., Mesures de la perfusion cérébrale chez le rat à l'aide de la RMN du $^{129}$Xe hyperpolarisé: étude de luids biologiques vecteurs du $^{129}$Xe, Comptes rendus de l'Académie des sciences, Paris, Chemie 4, 789-794 (2001).

[30] Wu, Z., Happer, W., Kitano, M., and Daniels, J. Experimental studies of wall interactions of adsorbed spin-polarized $^{131}$Xe nuclei. *Phys. Rev.* A. 42, 2774-2784 (1990).

[31] Zheng, Y., Low Field MRI and the Development of Polarized Nuclear Imaging (PNI)—A New Imaging Modality, Ph.D. thesis, University of Virginia (2014).

[32] Roemer, P. B., Edelstein, W. A., Hayes, C. E., Souza, S. P., and O. M. Mueller, O. M., The NMR Phased Array. *Magn. Reson. Med.* 16, 192-225 (1990).

[33] *Reaching for the Horizon: The* 2015 *Long Rang Plan for Nuclear Science,* publication of the U.S. Department of Energy, available at science.energy.gov.

[34] Stone, N. J., Table of nuclear magnetic dipole and electric quadrupole moments, *Atomic Data and Nuclear Data Tables* 90, 75-176 (2005).

[35] Atkins, T. M., Cassidy, M. C., Lee, M., Ganguly, S., Marcus, C. M. and Kauzlarich, S. M., Synthesis of Long $T_1$ Silicon Nanoparticles for Hyperpolarized $^{29}$Si Magnetic Resonance Imaging, ACS Nano 7, 1609-1617 (2004).

[36] Long, H. W. et al., High-Field Cross Polarization NMR from Laser-Polarized Xenon to a Polymer Surface, *J. Am. Chem. Soc.* 115, 8491-8492 (1993).

[37] Navon, G. et al., Enhancement of Solution NMR and MRI with Laser-Polarized Xenon, *Science* 271, 1848-1851 (1996).

[38] Moreno, K. M. et al., Transfer of hyperpolarization from long $T_1$ storage nuclei to short $T_1$ neighbors using FLOPSY-8, *Journal of Magnetic Resonance* 213, 187-191 (2011).

[39] Gatzke, M., Cates, G. D., Driehuys, B., Fox, D., Happer, W., and Saam, B., Extraordinarily Slow Nuclear Spin Relaxation in Frozen Laser-Polarized $^{129}$Xe, *Phys. Rev. Lett.* 70, 690-693 (1993).

[40] Schaefer, S. R., Cates, G. D., and Happer, W., Determination of spin-exchange parameters between optically pumped rubidium and $^{83}$Kr. Phys. Rev. A 41, 6063 (1990).

[41] Hossein-Zadeh, G. and Soltanian-Zadeh, H. DCT acquisition and reconstruction of MRI. Proc. SPIE, Vol. 3338, Medical Imaging 1998: Image Processing, ed. Kenneth M. Hanson, 398-407 (1998).

[42] Cates, G. D., White, D. J., Chien, T., Schaefer, S. R., Happer, W. Spin relaxation in gases due to inhomogeneous static and oscillating magnetic fields. *Phys. Rev. A.* 38, 5092 (1988).

[43] Driehuys, B., Cates, G. D., Miron, E., Sauer, K., Walter, D. K., Happer, W. High-volume production of laser-polarized $^{129}$Xe. Appl. Phys. Lett. 69:1668-1670 (1996).

[44] Ruset, I. C., Ketel, S., Hersman, F. W., Optical pumping system design for large production of hyperpolarized $^{129}$Xe. *Phys. Rev. Lett.* 96:053002 (2006).

What is claimed is:

1. A method for examining a target area of interest of a living subject, comprising:

polarizing nuclei of a radioactive substance such that the spins of the nuclei are oriented in a specific direction, to generate a polarized radioactive tracer with anisotropic gamma ray emission, wherein the radioactive substance is selected such that a degree of anisotropy is enhanced;

introducing the polarized radioactive tracer into a living subject for delivery to a target area of interest in the subject, wherein the polarized radioactive tracer is delivered such that nuclear spin relaxation of the polarized radioactive tracer is inhibited during transport of the polarized radioactive tracer to the target area of interest;

detecting gamma rays from the anisotropic gamma ray emission; and obtaining, from the detected gamma rays, at least one of imaging data and spectroscopic data associated with the tracer in the subject, wherein delivering the polarized radioactive tracer to the target area of interest such that nuclear spin relaxation of the polarized radioactive tracer is inhibited during transport comprises:

encapsulating the polarized radioactive tracer in microbubbles or nanobubbles and transporting the polarized radioactive tracer while encapsulated in the responsive microbubbles or nanobubbles; or embedding the polarized radioactive tracer in a nanoparticle and transporting the polarized radioactive tracer while embedded in the nanoparticle.

2. A system for examining a target area of interest of a living subject, comprising:

a polarizing system configured to polarize nuclei of a radioactive substance such that the spins of the nuclei are oriented in a specific direction, to generate a polarized radioactive tracer with anisotropic gamma ray emission, wherein the radioactive substance is selected such that degree of anisotropy is enhanced;

a delivery system configured to introduce the polarized radioactive tracer into a living subject for delivery to a target area of interest in the subject, wherein the polarized radioactive tracer is delivered such that nuclear spin relaxation of the tracer is inhibited during transport of the polarized radioactive tracer to the target area of interest;

at least one gamma detector configured to detect gamma rays from the anisotropic gamma ray emission; and a data acquisition system configured to obtain, from the detected gamma rays, at least one of imaging data and spectroscopic data associated with the tracer in the subject;

wherein delivering the polarized radioactive tracer to the target area of interest such that nuclear spin relaxation of the polarized radioactive tracer is inhibited during transport comprises:

encapsulating the polarized radioactive tracer in microbubbles or nanobubbles and transporting the polarized radioactive tracer while encapsulated in the responsive microbubbles or nanobubbles, or embedding the polarized radioactive tracer in a nanoparticle and transporting the polarized radioactive tracer while embedded in the nanoparticle.

* * * * *